(12) United States Patent
Gravesen et al.

(10) Patent No.: US 8,672,873 B2
(45) Date of Patent: Mar. 18, 2014

(54) MEDICINE DELIVERY DEVICE HAVING DETACHABLE PRESSURE SENSING UNIT

(75) Inventors: Peter Gravesen, Nordborg (DK); Heiko Arndt, Flensburg (DE); Serguei Chiriaev, Nordborg (DK)

(73) Assignee: Cequr SA, Horw (CH)

( * ) Notice: Subject to any disclaimer, the term of this patent is extended or adjusted under 35 U.S.C. 154(b) by 1096 days.

(21) Appl. No.: 12/542,808

(22) Filed: Aug. 18, 2009

(65) Prior Publication Data

US 2011/0046558 A1 Feb. 24, 2011

(51) Int. Cl.
*A61M 31/00* (2006.01)

(52) U.S. Cl.
USPC ............... 604/65; 604/67; 604/505

(58) Field of Classification Search
USPC ............. 604/67, 141, 180, 65, 890.1; 73/714; 340/522, 573.1, 603, 606, 611
See application file for complete search history.

(56) References Cited

U.S. PATENT DOCUMENTS

| | | | |
|---|---|---|---|
| 4,086,036 A | 4/1978 | Hagen et al. | |
| 4,237,775 A | 12/1980 | Eisele | |
| 4,435,173 A | 3/1984 | Siposs et al. | |
| 4,443,218 A * | 4/1984 | DeCant et al. | 604/67 |
| 4,551,133 A | 11/1985 | Zegers de Beyl et al. | |
| 4,617,014 A | 10/1986 | Cannon et al. | |
| 4,715,852 A | 12/1987 | Reinicke et al. | |
| 4,752,289 A | 6/1988 | Balding et al. | |
| 4,784,577 A | 11/1988 | Ritson et al. | |
| 4,784,645 A | 11/1988 | Fischell | |
| 4,836,752 A | 6/1989 | Burkett | |
| 4,898,579 A | 2/1990 | Groshong et al. | |
| 4,920,972 A | 5/1990 | Frank et al. | |
| 4,943,279 A | 7/1990 | Samiotes et al. | |
| 4,994,035 A | 2/1991 | Mokros | |
| 5,096,385 A | 3/1992 | Georgi et al. | |
| 5,190,522 A | 3/1993 | Wojcicki et al. | |
| 5,211,626 A | 5/1993 | Frank et al. | |
| 5,317,269 A | 5/1994 | Mills et al. | |
| 5,321,392 A | 6/1994 | Skakoon et al. | |
| 5,360,411 A | 11/1994 | Mimura et al. | |
| 5,395,320 A | 3/1995 | Padda et al. | |
| 5,492,533 A | 2/1996 | Kriesel | |
| 5,522,799 A | 6/1996 | Furukawa | |

(Continued)

FOREIGN PATENT DOCUMENTS

| | | |
|---|---|---|
| EP | 0 267 041 | 5/1988 |
| EP | 0 450 186 | 2/1995 |

(Continued)

OTHER PUBLICATIONS

International Search Report and Written Opinion mailed Jul. 20, 2011, for PCT Application PCT/US2010/044996, 18 pages.

*Primary Examiner* — Kami A Bosworth
*Assistant Examiner* — Imani Hayman
(74) *Attorney, Agent, or Firm* — Goodwin Procter LLP

(57) ABSTRACT

A fluid medicament delivery device includes a patient attachment unit and a separate indicator unit. The patient attachment unit includes a housing and a fluid channel located therein, wherein at least a portion of the fluid channel includes a flexible member substantially coterminous with the housing. The separate indicator unit is adapted to be detachably coupled to the housing of the patient attachment unit and includes a first sensing element for contacting the flexible member when the indicator unit is coupled to the housing to sense a flexure of the flexible member.

17 Claims, 14 Drawing Sheets

(56) References Cited

U.S. PATENT DOCUMENTS

| | | | |
|---|---|---|---|
| 5,524,907 A | 6/1996 | Walser | |
| 5,625,151 A | 4/1997 | Yamaguchi | |
| 5,681,284 A | 10/1997 | Herskowitz | |
| 5,720,721 A | 2/1998 | Dumas et al. | |
| 5,764,034 A | 6/1998 | Bowman et al. | |
| 5,791,880 A | 8/1998 | Wilson | |
| 5,839,467 A | 11/1998 | Saaski et al. | |
| 5,843,014 A | 12/1998 | Lattin et al. | |
| 5,897,530 A | 4/1999 | Jackson | |
| 5,928,194 A * | 7/1999 | Maget | 604/141 |
| 5,984,894 A | 11/1999 | Poulsen et al. | |
| 5,993,425 A | 11/1999 | Kriesel | |
| 6,009,752 A | 1/2000 | Iwata | |
| 6,358,225 B1 | 3/2002 | Butterfield | |
| 6,416,291 B1 | 7/2002 | Butterfield et al. | |
| 6,485,461 B1 | 11/2002 | Mason et al. | |
| 6,520,938 B1 | 2/2003 | Funderburk et al. | |
| 6,555,986 B2 | 4/2003 | Moberg | |
| 6,589,229 B1 * | 7/2003 | Connelly et al. | 604/890.1 |
| 6,647,860 B2 | 11/2003 | Savel et al. | |
| 6,656,158 B2 | 12/2003 | Mahoney et al. | |
| 6,656,159 B2 | 12/2003 | Flaherty | |
| 6,659,980 B2 | 12/2003 | Moberg et al. | |
| 6,669,669 B2 | 12/2003 | Flaherty et al. | |
| 6,692,457 B2 | 2/2004 | Flaherty | |
| 6,699,218 B2 | 3/2004 | Flaherty et al. | |
| 6,723,072 B2 | 4/2004 | Mahoney et al. | |
| 6,740,059 B2 | 5/2004 | Flaherty | |
| 6,749,587 B2 | 6/2004 | Flaherty | |
| 6,768,425 B2 | 7/2004 | Flaherty et al. | |
| 6,830,558 B2 | 12/2004 | Flaherty et al. | |
| 6,852,094 B2 | 2/2005 | Beck et al. | |
| 6,852,104 B2 | 2/2005 | Blomquist | |
| 6,871,546 B2 | 3/2005 | Scheurich et al. | |
| 6,892,755 B2 | 5/2005 | Black | |
| 6,901,293 B2 | 5/2005 | Rogers et al. | |
| 6,960,192 B1 | 11/2005 | Flaherty et al. | |
| 7,000,806 B2 | 2/2006 | Py et al. | |
| 7,018,360 B2 | 3/2006 | Flaherty et al. | |
| 7,029,455 B2 | 4/2006 | Flaherty | |
| 7,066,031 B2 | 6/2006 | Zdeblick et al. | |
| 7,109,878 B2 | 9/2006 | Mann et al. | |
| 7,137,964 B2 | 11/2006 | Flaherty | |
| 7,144,384 B2 | 12/2006 | Gorman et al. | |
| 7,291,126 B2 | 11/2007 | Shekalim et al. | |
| 7,303,549 B2 | 12/2007 | Flaherty et al. | |
| 7,341,572 B2 | 3/2008 | Bridle et al. | |
| 7,377,907 B2 | 5/2008 | Shekalim | |
| 7,771,412 B2 | 8/2010 | Anderson et al. | |
| 7,887,505 B2 | 2/2011 | Flaherty | |
| 7,918,825 B2 | 4/2011 | O'Connor et al. | |
| 2002/0087147 A1 | 7/2002 | Hooper et al. | |
| 2002/0161332 A1 | 10/2002 | Ramey | |
| 2002/0183693 A1 | 12/2002 | Peterson et al. | |
| 2003/0204274 A1 | 10/2003 | Ullestad et al. | |
| 2004/0133166 A1 | 7/2004 | Moberg et al. | |
| 2004/0158207 A1 | 8/2004 | Hunn et al. | |
| 2004/0167464 A1 | 8/2004 | Ireland et al. | |
| 2004/0216103 A1 | 10/2004 | Burky et al. | |
| 2005/0101932 A1 | 5/2005 | Cote et al. | |
| 2005/0109115 A1 * | 5/2005 | Gatesman | 73/753 |
| 2005/0171512 A1 | 8/2005 | Flaherty | |
| 2005/0182366 A1 | 8/2005 | Vogt et al. | |
| 2005/0203461 A1 | 9/2005 | Flaherty et al. | |
| 2005/0238507 A1 | 10/2005 | DiIanni et al. | |
| 2005/0266582 A1 | 12/2005 | Modlin et al. | |
| 2006/0030836 A1 | 2/2006 | Lee et al. | |
| 2006/0041229 A1 | 2/2006 | Garibotto et al. | |
| 2006/0161108 A1 | 7/2006 | Mogensen et al. | |
| 2006/0178633 A1 | 8/2006 | Garibotto et al. | |
| 2006/0184121 A1 | 8/2006 | Brockman et al. | |
| 2006/0282290 A1 | 12/2006 | Flaherty et al. | |
| 2007/0074722 A1 | 4/2007 | Giroux et al. | |
| 2007/0083153 A1 | 4/2007 | Haar | |
| 2007/0112301 A1 | 5/2007 | Preuthun et al. | |
| 2007/0118405 A1 | 5/2007 | Campbell et al. | |
| 2007/0231204 A1 | 10/2007 | Hyde et al. | |
| 2007/0250007 A1 | 10/2007 | Shekalim | |
| 2008/0033361 A1 | 2/2008 | Evans et al. | |
| 2008/0051710 A1 | 2/2008 | Moberg et al. | |
| 2008/0051738 A1 | 2/2008 | Griffin | |
| 2008/0086086 A1 | 4/2008 | Field et al. | |
| 2008/0116647 A1 | 5/2008 | Anderson et al. | |
| 2008/0119822 A1 | 5/2008 | Knauper | |
| 2008/0139907 A1 | 6/2008 | Rao et al. | |
| 2008/0147044 A1 | 6/2008 | Palmer et al. | |
| 2008/0147050 A1 | 6/2008 | Mann et al. | |
| 2008/0160492 A1 | 7/2008 | Campbell et al. | |
| 2008/0172030 A1 | 7/2008 | Blomquist | |
| 2008/0183060 A1 | 7/2008 | Steil et al. | |
| 2008/0214919 A1 | 9/2008 | Harmon et al. | |
| 2008/0227210 A1 | 9/2008 | Smith | |
| 2008/0234630 A1 | 9/2008 | Iddan et al. | |
| 2008/0294094 A1 | 11/2008 | Mhatre et al. | |
| 2009/0099521 A1 | 4/2009 | Gravesen et al. | |
| 2009/0143732 A1 | 6/2009 | O'Connor et al. | |
| 2010/0017141 A1 | 1/2010 | Campbell et al. | |
| 2011/0043357 A1 | 2/2011 | Peatfield et al. | |
| 2011/0056301 A1 * | 3/2011 | Winkler et al. | 73/714 |

FOREIGN PATENT DOCUMENTS

| | | |
|---|---|---|
| EP | 1177802 | 2/2002 |
| EP | 1 792 655 | 6/2007 |
| GB | 2 031 558 | 4/1980 |
| WO | WO-93/18305 | 9/1993 |
| WO | WO-9427669 A1 | 12/1994 |
| WO | WO-9738322 A1 | 10/1997 |
| WO | WO-99/01731 | 1/1999 |
| WO | WO-02/070047 | 9/2002 |
| WO | WO-02068015 | 9/2002 |
| WO | WO-2007/057038 | 5/2007 |
| WO | WO-2008017329 | 2/2008 |
| WO | WO-2008024810 | 2/2008 |

* cited by examiner

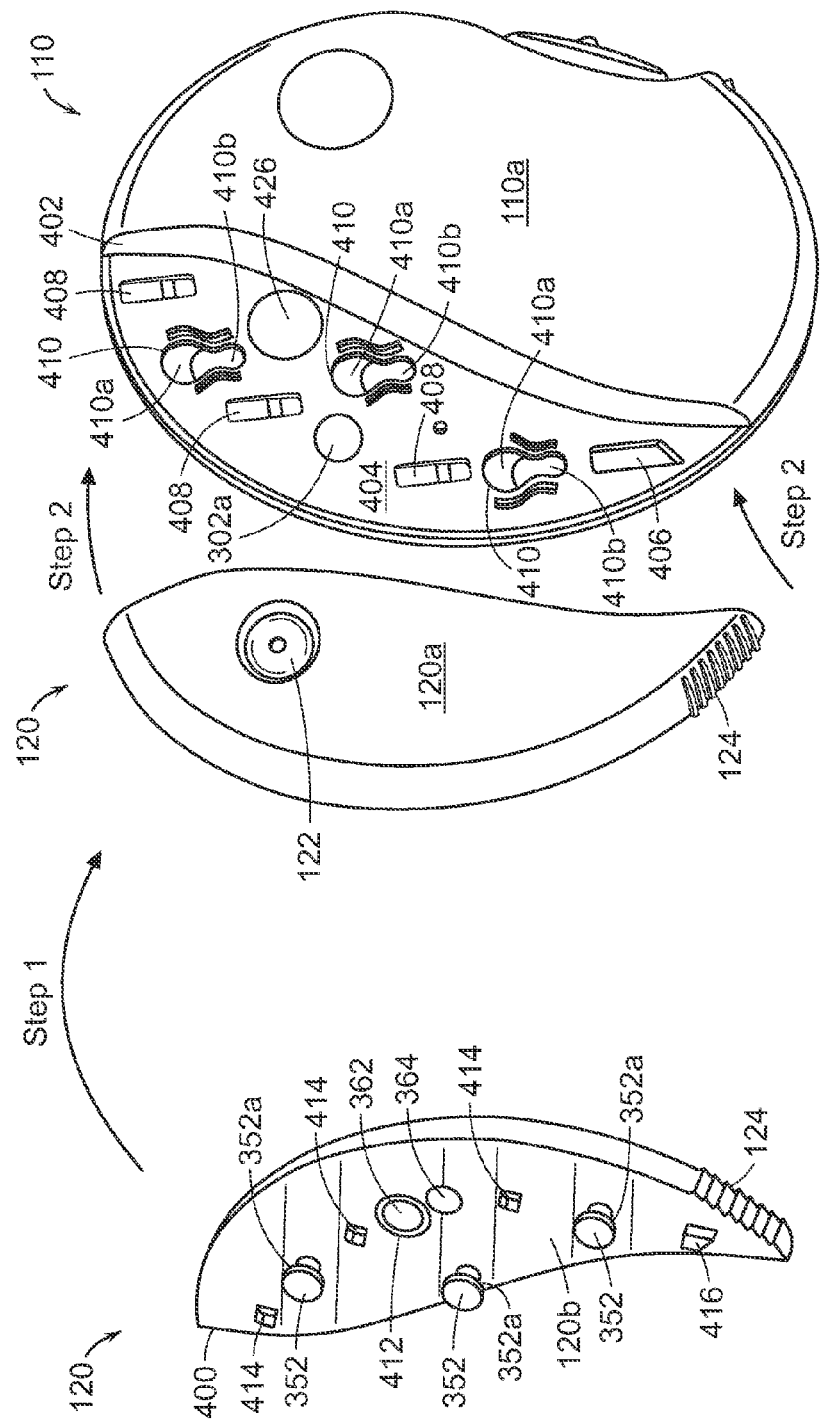

MEDICINE DELIVERY DEVICE HAVING DETACHABLE PRESSURE SENSING UNIT

FIELD OF THE INVENTION

This invention relates generally to medicament delivery devices and, more specifically, to medicament infusion devices that utilize a reusable indicator unit and a disposable medicament-delivery unit.

BACKGROUND

Medicament infusion devices are utilized to deliver liquid fluid medicine to patients. For example, insulin infusion devices are often used by persons with diabetes to maintain adequate insulin levels throughout the day or to increase insulin levels during mealtime. These insulin infusion devices can replace the syringe-based injections common among those with diabetes.

Insulin infusion devices are available in several forms, and include several common components. Generally, an infusion device includes a housing that may be worn on a patient's clothing (a belt, for example) or on the patient himself, and that contains a number of mechanical and electrical components. A reservoir holds the insulin and an electro-mechanical pump mechanism (various types are used) delivers the insulin as needed to the patient. Battery-powered electronics control the pump and ensure that the device is operating properly. Various sensors communicate with the electronics and other components to detect occlusions, sound alarms, measure remaining insulin capacity, etc.

While these devices are useful, they do suffer from several shortcomings. First, the high expense of the devices makes them accessible to fewer people than the diabetic population members who may benefit from their use. Second, failure or malfunction of one component requires repair or replacement of the entire device, a costly scenario. For example, if the pump fails, often the entire unit (including the properly functioning—and expensive—electronics) must be replaced. Third, over time the device gets dirty due to repeated uses, which requires periodic cleaning and may cause a failure condition at a later date.

SUMMARY OF THE INVENTION

What is needed, then, is a medicament infusion device that utilizes low-cost components, some of which may be replaced periodically after use, without having to dispose of other expensive, but operational, components in the device.

In one aspect, the invention relates to a fluid medicament delivery device having a patient attachment unit that includes a housing and a fluid channel located therein, such that at least a portion of the fluid channel has a flexible member substantially coterminous with the housing. The fluid medicament delivery device includes a separate indicator unit adapted to be detachably coupled to the housing of the patient attachment unit. The indicator unit includes a first sensing element for contacting the flexible member when the indicator unit is coupled to the housing, such that the first sensing element senses a flexure of the flexible member. In an embodiment of the foregoing aspect, the indicator unit also includes a second sensing element for sensing a pressure external to the housing. In another embodiment, the pressure external to the housing includes an ambient pressure.

In an embodiment of the above aspect, the first sensing element includes a pressure sensor. In another embodiment, the first sensing element also includes at least one of a fluid and a gel adapted to contact the flexible member, such that the flexure of the flexible member is transmitted by the at least one of the fluid and the gel to the pressure sensor. In yet another embodiment, the separate indicator unit defines a well for containing at least one of the liquid and the gel. In still another embodiment, the separate indicator unit includes a raised lip surrounding the well, such that the raised lip is disposed above a proximate portion of the separate indicator unit. In another embodiment, the raised lip is adapted to contact the housing of the patient attachment unit.

In another embodiment of the above aspect, the second sensing element includes a pressure sensor adapted to sense the pressure external to the housing, and at least one of a fluid and a gel adapted to transmit the pressure external to the housing to the pressure sensor. In an embodiment, the housing has a hermetically-sealed housing defining an interior space and including at least one substantially flexible housing portion. The substantially flexible housing portion is adapted for transmitting the pressure external to the housing to the interior space. In still another embodiment, the substantially flexible housing portion is located on a portion of the patient attachment unit facing the separate indicator unit and the second sensing element is located on a portion of the separate indicator unit facing the patient attachment unit, when the patient attachment unit is coupled to the separate indicator unit.

In yet another embodiment of the foregoing aspect, the patient attachment unit is adapted for adhesion to a skin surface of a patient. In an embodiment, the fluid medicament delivery device also includes a processor adapted for interpreting a signal from a pressure sensor, such that the signal is sent to the processor based at least in part on the flexure of the flexible member.

In another aspect, the invention relates to a method of monitoring pressure within a fluid channel of a fluid medicament delivery device, the method including measuring an actual pressure of a fluid within the fluid channel, comparing the actual pressure to a pressure range including a maximum pressure and a minimum pressure, and sending a notification when the actual pressure is outside of the pressure range. In an embodiment, the method also includes measuring a pressure external to the fluid medicament delivery device.

In an embodiment of the above aspect, the method of monitoring pressure within a fluid channel of a fluid medicament delivery device also includes modifying the actual pressure based on the external pressure to obtain a corrected pressure, and comparing the corrected pressure to the pressure range. In another embodiment, the method also includes modifying the maximum pressure and a minimum pressure of the pressure range based on the external pressure to obtain a corrected pressure range, and comparing the corrected pressure range to the actual pressure. In still another embodiment, when the actual pressure exceeds the maximum pressure, the notification includes at least one of a downstream occlusion notification and a near-empty reservoir notification. In yet another embodiment, when the actual pressure is less than the minimum pressure, the notification includes at least one of an upstream occlusion notification and an empty reservoir notification.

In another aspect, the invention relates to a method of manufacturing a pressure sensing element, the method including securing a pressure sensor to a base, securing a template defining a well therein to the base, such that the pressure sensor is located in a bottom portion of the well. The method includes filling at least partially the well with a gel having a substantially liquid state, so that the well includes a filled portion and an unfilled portion, and the filled portion and the unfilled portion are characterized by a presence or an absence of gel. The method includes solidifying the gel in the filled portion to a substantially gelled state, and filling the unfilled portion with a gel having a substantially liquid state.

BRIEF DESCRIPTION OF THE FIGURES

Other features and advantages of the present invention, as well as the invention itself, can be more fully understood from the following description of the various embodiments, when read together with the accompanying drawings, in which:

FIGS. 9A-9D depict a procedure for mounting the indicator unit to the patient attachment unit in accordance with one embodiment of the present invention;

DETAILED DESCRIPTION

Figure 1:
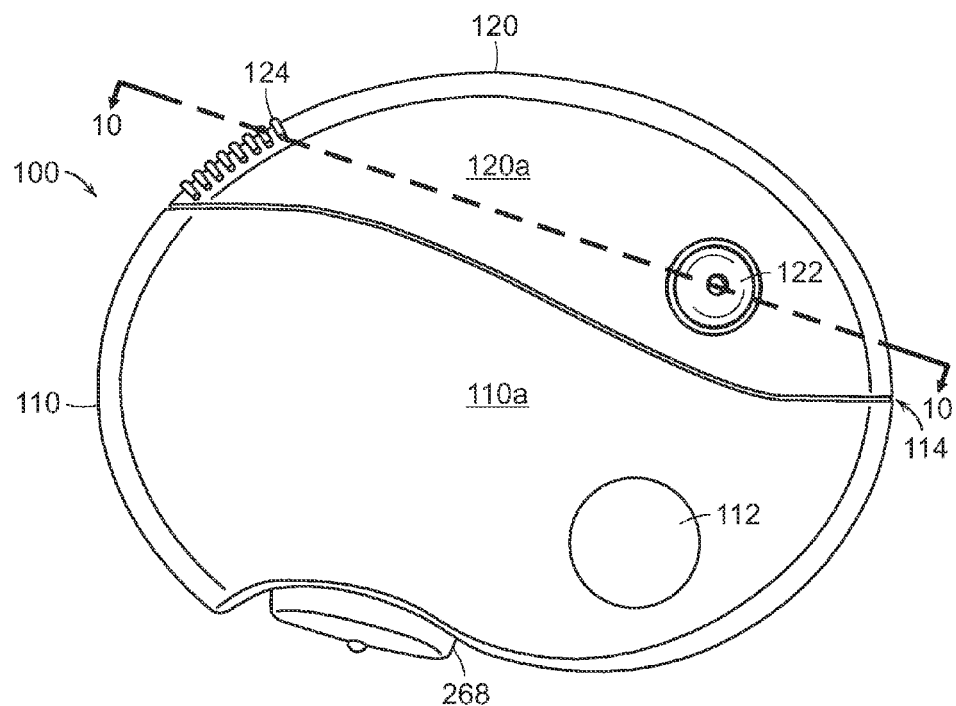
FIG. 1 is a schematic top view of a fluid medicament delivery device in accordance with one embodiment of the invention.
Figure 2:
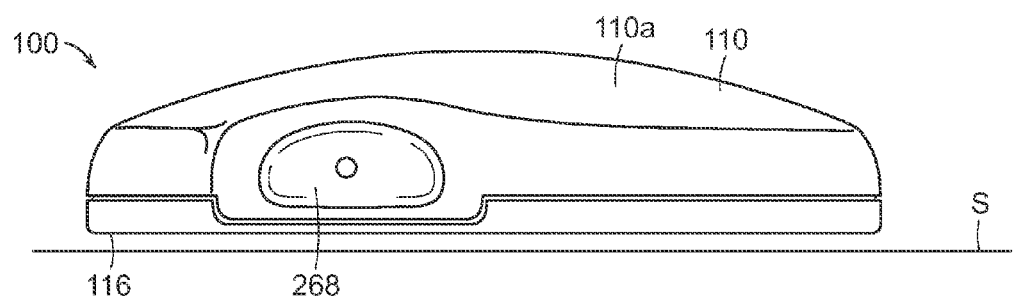
FIG. 2 is a schematic side view of the fluid medicament delivery device of FIG. 1.

FIGS. 1 and 2 depict an embodiment of an assembled fluid medicament delivery device 100 having at least two modules, a patient attachment unit 110 and a separate indicator unit 120, each having a housing 110a, 120a, respectively. The depicted fluid medicament delivery device 100, when assembled, defines a substantially oval shape, although other shapes (circular, oblong, elliptical, etc.) are also contemplated. In general, an assembled device having round corners, smooth edges, etc., may be desirable, since the device is designed to be worn on the skin of a patient, underneath clothing. Other aspects of the device that make it generally unobtrusive during wear include a small size (only about several inches across) and a low profile. Other device shapes and sizes are also contemplated.

The patient attachment unit 110 includes a bolus button 268 for delivering a dose of fluid medicament, as described below. A cannula insertion device (See FIG. 13A) inserts a cannula through the device 110, subcutaneously through the skin S of a patient. Cannula insertion devices are described in U.S. patent application Ser. No. 12/250,760, filed Oct. 14, 2008, the disclosure of which is hereby incorporated by reference herein in its entirety. After insertion, the cannula insertion device is disconnected from the patient attachment unit 110, and a cap 112 is used to seal the opening to prevent ingress of contaminants, moisture, etc. The separate indicator unit 120 includes an indicator button 122. A textured edge 124, may be present on all or part of the edge of the housing 120a to provide a gripping surface during attachment and/or disconnection of the indicator unit 120 and the patient attachment unit 110, as described in more detail below. Alternatively or additionally, the edge of patient attachment unit housing 110a may also be textured.

The patient attachment unit 110 is connected to and in communication with the separate indicator unit 120, as described in more detail below. The housings 110a, 120b of the patient attachment unit 110 and the indicator unit 120 meet at a curved interface 114. Interfaces having other mating shapes are also contemplated. The bottom surface of the patient attachment unit 110 includes a patient attachment interface 116. The patient attachment interface 116 may include one or more adhesive pads secured to the bottom surface of the patient attachment unit 110 for adhering the fluid medicament delivery device 100 to the skin S of a patient during use. The interface 116 may comprise any suitable configuration to adhere the patient attachment unit 110 to the skin S. In one embodiment, the interface 116 includes a plurality of discrete points of attachment. Other embodiments utilize concentric adhesive circles or ovals.

The indicator button 122 may be used by the patient to test the functioning of the fluid medicament delivery device 100 or to cancel a notification presently being delivered or to prompt for a repetition of a previous message or other information stored by the indicator unit. Actuating the indicator button 122 may initiate one or more tests to indicate to the patient various operational or therapy states of the device 100, such as whether the separate indicator unit 120 is properly mounted to the patient attachment unit 110, whether an internal battery has sufficient power for continued use, and/or whether pressure sensing within the device 110 is operating properly. Other tests are also contemplated. A single indicator button, such as that depicted in FIG. 1, may be used to run one or more tests. The medicament delivery device 100 may be programmed to recognize patterns of actuations of the indicator button to initiate certain test routines. That is, two actuations in quick succession may initiate a "Battery Power Available" test routine, three actuations in quick succession may initiate a "Pressure Sensor Check" test routine, etc. Other combinations of short actuations and long actuations (e.g., Short, Long, Short; Long, Long, Short, etc.) are also contemplated to initiate any number of test routines. Alternatively or additionally, two or more buttons or other input features may be included on the device, for initiating one or more separate tests. Positive or negative feedback of the test results may be provided to the patient in the form of audible sounds of differing tones or durations, illumination/delumination of lights, vibrations, and combinations thereof. In certain embodiments, light emitting diodes (LEDs) may be used to illuminate the button itself or may illuminate portions of the indicator unit housing to provide feedback to the patient. Graphical indicia or alphanumeric information may be displayed on a suitable output device.

Figure 3:
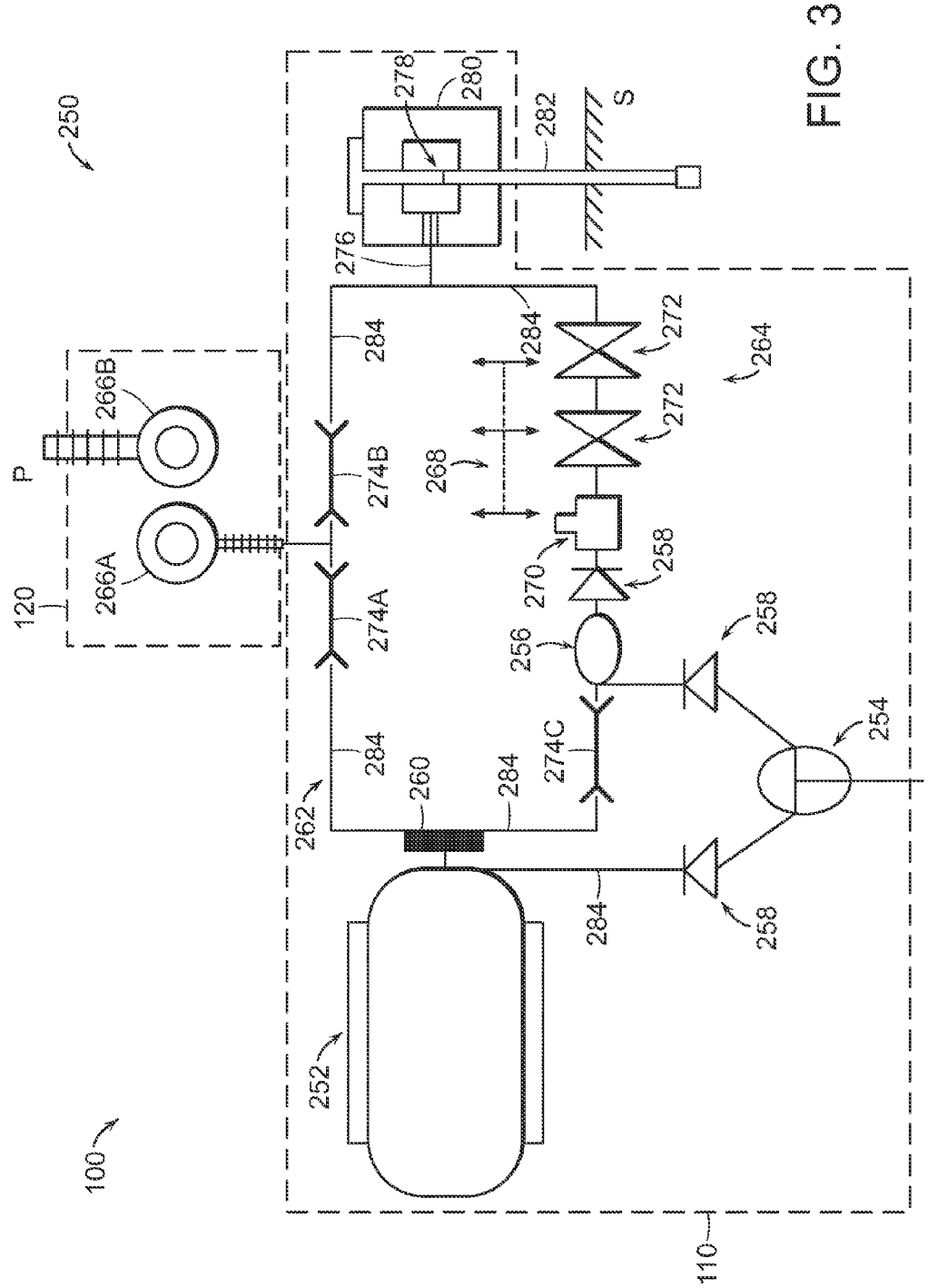
FIG. 3 is a schematic diagram of an exemplary infusion device micro-fluidic circuit in accordance with one embodiment of the invention.

FIG. 3 is a schematic diagram of an exemplary infusion device micro-fluidic circuit 250 that may be incorporated into the fluid medicament delivery device 100 described herein. Other infusion devices having micro-fluidic circuits are described in U.S. Patent Application Publication No. 2005/0165384, published Jul. 28, 2005, the disclosure of which is hereby incorporated by reference herein in its entirety. The micro-fluidic circuit 250 includes a pressurized reservoir 252 that is, in this case, an elastomer bladder. Alternatively, a flexible vessel or bag compressed by a spring may be utilized. A fill port 254 is used to introduce fluid, such as insulin, to the micro-fluidic circuit 250. In this micro-fluidic circuit 250, introducing insulin via the fill port 254 fills both the reservoir 252 and a variable-volume bolus reservoir 256. Check valves 258 prevent backflow of insulin in a number of locations.

During use, insulin is forced from the reservoir 252 by elastic contraction of the elastomer, through a filter 260, and into two parallel flowpaths, a basal flowpath 262 and a bolus flowpath 264. The basal flowpath 262 delivers a constant dose or steady-state level of insulin to a patient; the bolus flowpath 264 delivers a bolus dose of insulin to the patient as needed or desired by the patient, for example, in conjunction with a meal. The basal flowpath 262 includes a first pressure sensor 266A or other pressure or flow sensors in communication with the flowpath 262, for example, at a mid-point in the basal flowpath. In an alternative embodiment, the first pressure sensor 266A or first sensing element 262 may be placed further upstream or downstream in the basal flowpath, as desired. In another alternative embodiment, a plurality of pressure sensors in communication with the basal flowpath 262 may be utilized. A second pressure sensor 266B or second sensing element is exposed to ambient air pressure P. The function of and relationship between the pressure sensors 266A, 266B is described in more detail below. In one embodiment, the pressure sensors 266A, 266B consist of micro-electronic-mechanical system (MEMS) sensors. Each MEMS sensor is about 2 mm square but sensors having different dimensions may also be used. Both MEMS sensors are contained within the indicator unit 120. In FIG. 3, the pressure sensor 266A communicates with a portion of the basal circuit 262 between two flow restrictors 274A, 274B (e.g., microcapillaries). In one embodiment, this portion between the flow restrictors 274A, 274B may be a pressure sensor chamber, as described in more detail below. The pressure sensor 266A senses pressure changes in the basal flowpath 262, which may be indicative of occlusion conditions that increase pressure therein. The pressure sensor 266B senses changes in ambient air pressure external to the fluid medicament delivery device 100. The pressure sensors 266A, 266B are absolute pressure sensors, but a single relative pressure sensor may also be utilized. A relative pressure sensor, e.g., a gauge MEMS sensor, may be used to replace both absolute pressure sensors.

To deliver a bolus via the bolus flowpath 264, the patient presses a button 268 that drives a single stroke (delivering a single dose) of a bolus displacement chamber 270 and opens two valves 272. The valves 272 are in series for redundancy safety purposes. An optional flow restrictor 274C regulates, in part, the fluid flow through the bolus flowpath 264. The parallel flowpaths 262, 264 join at a common channel 276 just before an internal chamber or a cannula void 278. The cannula void 278 is formed in a cannula base 280, which allows a point of connection to a cannula 282. The cannula 282 extends below the skin S of a patient, thus delivering the insulin subcutaneously. In one embodiment, the actuation of the bolus button 268 may be sensed by the indicator unit 120 with, for example, a magnetic sensor, a Hall effect sensor, or a switch. In an alternative embodiment of the present invention, at least one pressure sensor may be placed in the bolus flowpath 264, thereby allowing the indicator unit 120 to sense the actuation of the bolus button 268. Conduits 284 having diameters larger than those of the flow restrictors 274A, 274B, 274C connect the various components.

Figure 4:
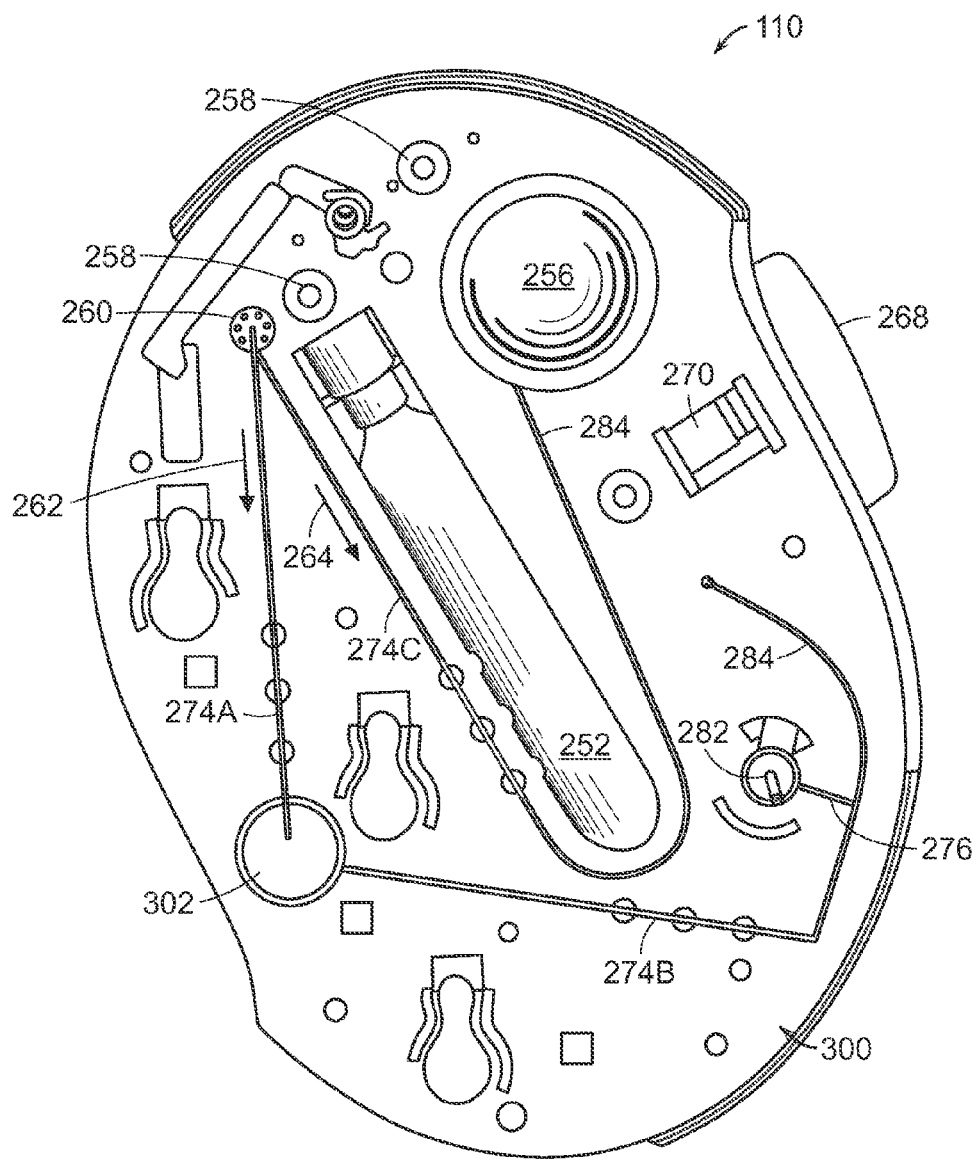
FIG. 4 is a schematic bottom view of a patient attachment unit of the fluid medicament delivery device of FIG. 1 with an external housing removed.

FIG. 4 depicts a bottom view of the patient attachment unit 110 showing the internal components and structures therein, with the housing removed. Specifically, the bottom portion of the housing 110a, to which the attachment interface 116 is secured, has been removed. These internal components and structures correspond generally to the micro-fluidic circuit 250, discussed in FIG. 3. The components and structures in the patient attachment unit 110 may be disposed in or connected to a flow manifold 300, which serves as a mounting platform for the various components. Note that not all conduits and flow components are depicted in FIG. 4, as some components may be secured to the opposite side of the manifold 300 or formed therein.

As described above with regard to FIG. 3, insulin in the bolus flowpath 264 (the bolus flowpath 264, in FIG. 4, is downstream of the labeled arrow) of the micro-fluidic circuit 250 is delivered from the elastomer reservoir 252, filtered through the filter 260, and stored in the variable-volume bolus reservoir 256. In certain embodiment, the elastomer reservoir 252 may have a total volume of about 3200 microliters; the variable-volume bolus reservoir 256 may have a total volume of about 180 microliters to about 260 microliters. Other volumes of the various components are also contemplated. When the fluid pressure in the elastomer reservoir 252 is greater than the fluid pressure in the variable-volume reservoir 256, the variable-volume reservoir 256 will continue to fill, subject to the flow rate dictated at least by flow restrictor 274C in the bolus flowpath 264. Downstream of the variable-volume bolus reservoir 256 is the bolus displacement chamber 270, which may store a single dose of insulin (e.g., about 5, about 10, about 20, or about 25, or greater than about 25 microliters of insulin, in various embodiments). A check valve 258 allows for free flow of insulin from the variable-volume bolus reservoir 256 to the bolus displacement chamber 270. The check valve 258 prevents backflow during a bolus stroke (i.e., actuation of the bolus button 268).

Actuating the bolus button 268 opens the two valves 272 (See FIG. 3) and empties the entire contents of the bolus displacement chamber 270. Audible, visual, and/or tactile feedback may be provided to the patient to signal that a bolus has been delivered. Releasing the bolus button 268 closes the two downstream valves 272. The displacement chamber 270 is then refilled with insulin from the variable-volume bolus reservoir 256, which is, in turn, filled with insulin from the reservoir 252. The bolus flow rate is controlled with a fixed volume-per-stroke of bolus stimulus, i.e., a predetermined volume of insulin-per-stroke. In another embodiment, the bolus flow control rate also may be controlled by a bolus rate flow restrictor. Also, downstream of the filter 260 is the basal flowpath 262 (the basal flowpath 262, in FIG. 4, is downstream of the labeled arrow) of the micro-fluidic circuit 250. The flow restrictors 274A, 274B are located on opposite sides of a pressure sensor chamber 302.

In various embodiments, each flow restrictor 274A, 274B has a length in a range of about 18 mm to about 35 mm. Other lengths of the flow restrictors are also contemplated, for example, from about 10 mm to about 20 mm. The various channels 284 in the manifold 300 may be formed by, for example, laser cutting, and the flow restrictors 274A, 274B may be placed therein. The flow restrictors 274A, 274B may be glued or fused into the channels, though other methods of retention are also contemplated. Exemplary flow restrictors are described in U.S. Patent Application Publication No. 2006/0054230, the disclosure of which is hereby incorporated by reference herein in its entirety. The flow restrictors 274A, 274B are connected to and in fluidic communication with a pressure sensor chamber 302 that includes a flexible member or sensor membrane 302a (See FIG. 7) disposed thereon. The sensor membrane 302a may be generally coterminous with a mating mounting platform 404 (See FIG. 7) of the patient attachment unit 110, as described in more detail below. As the insulin in the basal flowpath 262 flows into the chamber 302, pressure of the insulin within the basal flowpath 262 displaces the sensor membrane 302a. This displacement is sensed by the pressure sensor 266A, as described below. In this manner, the pressure sensor 266A may sense the pressure of the insulin in the basal flowpath via movement of the sensor membrane 302a.

Figure 5:
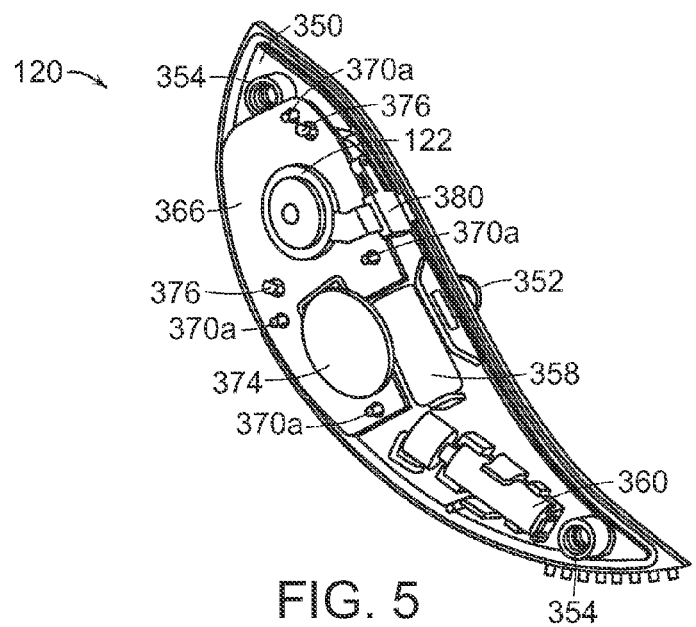
FIG. 5 is a schematic perspective view of an indicator unit of the fluid medicament delivery device of FIG. 1 with an external housing removed.
Figure 6:
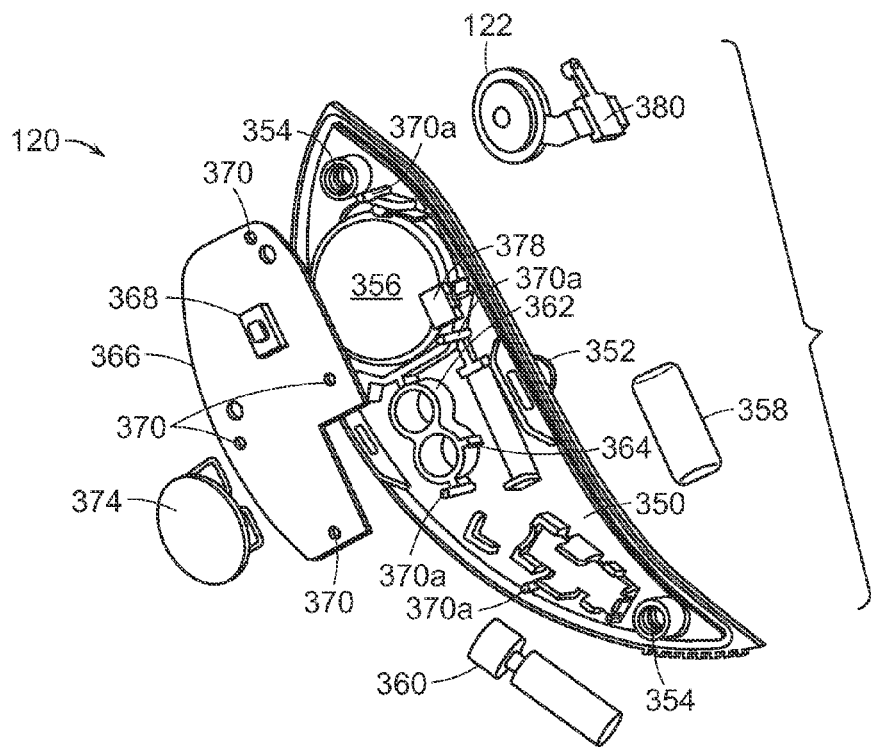
FIG. 6 is a schematic exploded perspective view of the indicator unit of FIG. 5.

FIG. 5 depicts a schematic perspective view of the indicator unit 120 with the top exterior housing 120a removed. FIG. 6 shows an exploded view of the indicator unit 120 depicted in FIG. 5. As discussed herein, the indicator unit 120 may, in certain embodiments, detect changes in pressure within the micro-fluidic circuit 250 contained in the patient attachment unit 110, and perform other tests to ensure proper operation of the medicine delivery device 100. The patient may be alerted as necessary via audible, visual, and/or tactile (e.g., vibration) signals. The components to detect pressure changes, process information, and generate signals or alerts to the patient are contained within the indicator unit 120.

The internal components of the separate indicator unit 120 are mounted, either directly or indirectly, to a mounting platform 350, which, in one embodiment, may be the bottom surface of the indicator unit 120. Partially shown extending from the underside of the indicator unit 120 is at least one circular mating projection 352, which is configured to mate with the patient attachment unit 110, as described below. Mounting arms 354 defining hollow interiors are disposed at or near the edges of the mounting platform 350. The mounting arms 354 correspond to and connect to the top exterior housing 120a with screw, snap-fit, press or other types of connections. Also disposed on the mounting platform 350 are a supercapacitor 358, a vibrating motor 360, and two wells 362, 364. Each well 362, 364 defines a hollow geometrical structure, e.g., a cylinder. Overlaid on at least the wells 362, 364 is a printed circuit board (PCB) 366, which may include one or more processors, as well as a test switch 368 disposed thereon. Several apertures 370 formed in the PCB 366 correspond to and align with extensions 370a from the mounting platform 350. The extensions 370a may be melted during manufacturing to secure the PCB 366 thereto. The indicator button 122 aligns vertically over the test switch 368. A piezoelectric sounder 374 or other sound-generating component is located proximate the PCB 366. One or more battery holder solder pins 376 also penetrate the PCB. An activation switch 378 interacts with an activation button 380, which contacts an activation projection 428 (FIG. 7) on the patient attachment unit 110.

Figure 7:
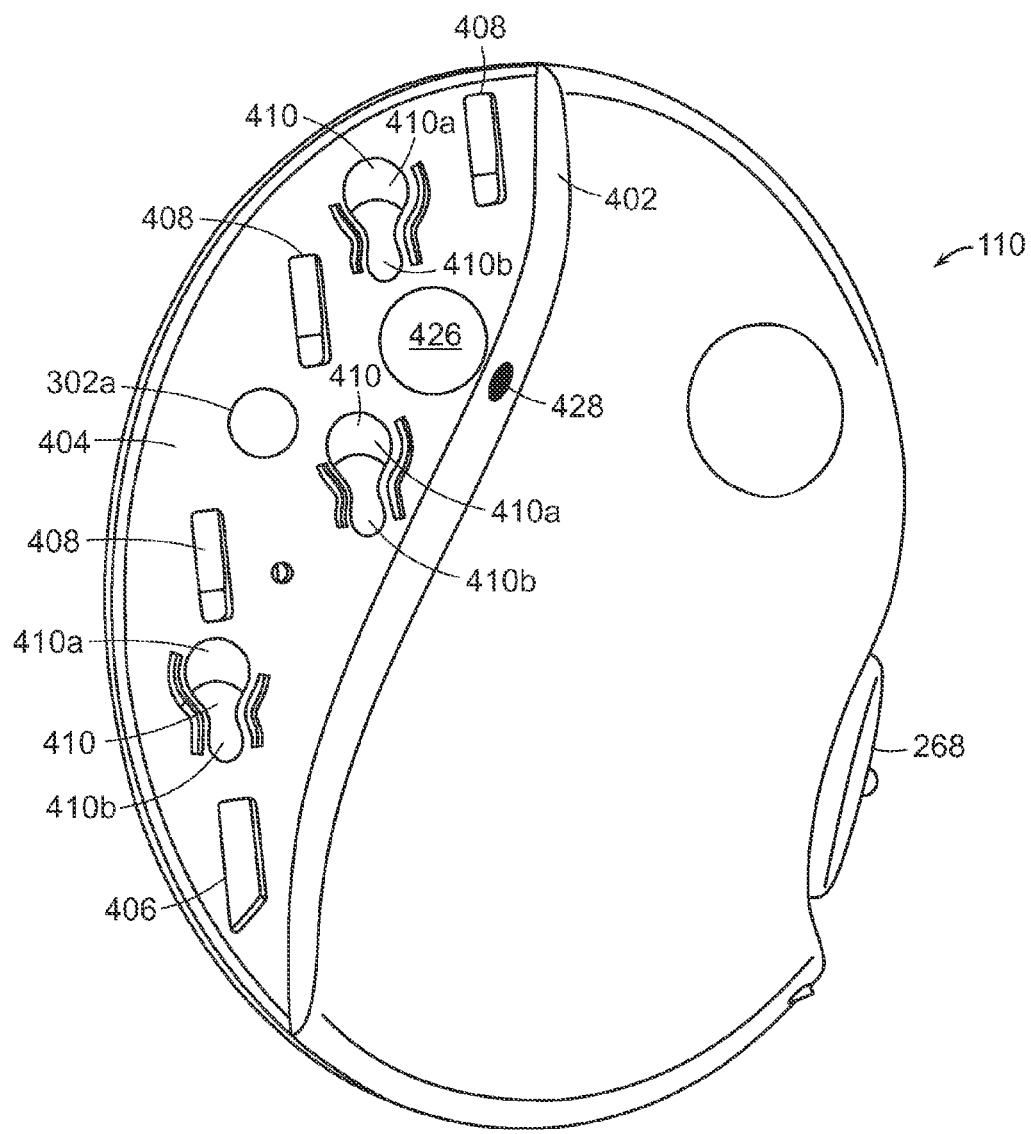
FIG. 7 is a schematic top view of the patient attachment unit of the fluid medicament delivery device of FIG. 1.
Figure 8:
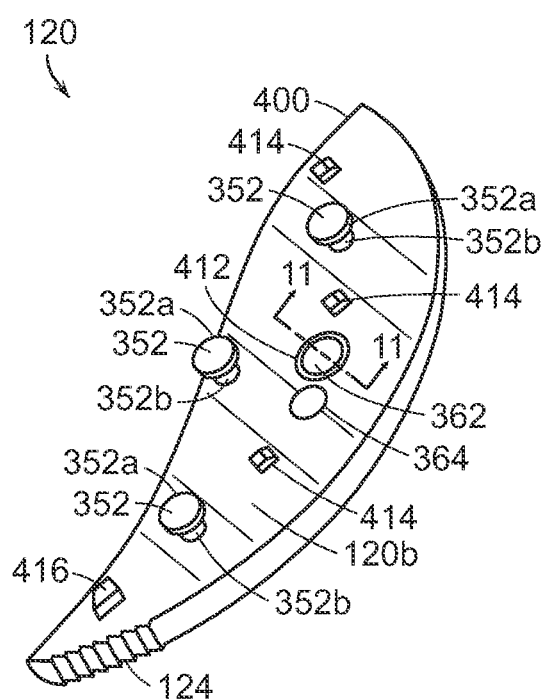
FIG. 8 is a schematic bottom perspective view of the indicator unit of the fluid medicament delivery device of FIG. 1.

FIG. 7 depicts the patient attachment unit 110 and FIG. 8 depicts the underside of the indicator unit 120. The elements that allow for the connection and communication between both units 110, 120 are described below. Indicator unit 120 has a contoured surface 400 that mates with a matching surface 402 of the patient attachment unit 110. The surfaces may be of a undulating curved shape, as shown. Alternative embodiments may utilize crescent, linear, or other shaped surfaces. In another embodiment of the present invention, the contoured surface 400 of the indicator unit 120 may have a vertically-graded slope. The mating shapes of the leading surface 400 and the matching surface 402 assist in properly securing and aligning the indicator unit 120 to the patient attachment unit 110 and help prevent inadvertent detachment of the two units. Further, the complementary shapes of the contoured surface 400 and the matching surface 402 direct the indicator unit 120 to move in and out of a locking position, to connect and disconnect the indicator unit 120 from the patient attachment unit 110 while ensuring proper alignment of the operative components.

Proximate the matching surface 402 of the patient attachment unit 110 is a mating mounting platform 404. Multiple apertures 406, 408, and 410 in the mounting platform 404 are configured to receive corresponding mating projections 416, 414, 352 extending from a bottom surface 120b of the indicator unit 120 to secure the two units. The apertures 406, 408, and 410 may have a polygon, oblong, or other shape. Alternative configurations, shapes, and orientations of the apertures 406, 408, 410 and the mating projections 416, 414, 352 are contemplated. The wells 362, 364 are formed in and are substantially coterminous with the bottom surface 120b of the indicator unit 120. In addition, a raised lip 412 circumscribes the well 362 and projects above the bottom surface 120b. The well 362 and the lip 412 are oriented to substantially align with the sensor membrane 302a when the patient attachment unit 110 and indicator unit 120 are connected. The sensor membrane 302a is substantially coterminous with the mating mounting platform 404, and is the top surface of the pressure chamber 302, described above. A pressure equalizing membrane 426 also may be substantially coterminous with the mating mounting platform 404. The function of the pressure equalizing membrane 426 is described below. The activation projection 428 contacts the activation button 380 when the patient attachment unit 110 is connected to the indicator unit 120.

Each of the projections 416, 414, 352 of the indicator unit 120 mate with the corresponding apertures 406, 408, and 410 of the patient attachment unit 110 to form the complete assembled fluid medicament delivery device 100. Specifically, the guiding projection 416 mates with the guiding aperture 406; the aligning projections 414 mate with the aligning apertures 408; and the circular mating projections 352 mate with the asymmetrically oblong apertures 410. Each mating pair has corresponding shapes and corresponding orientations to secure the indicator unit 120 to the patient attachment unit 110. Each of the circular mating projection 352 includes an enlarged end 352a, which is enlarged relative to an extension 352b that projects from the exposed bottom surface 120b of the indicator unit 120. The enlarged end 352a is configured and sized to fit within the enlarged portion 410a of aperture 410. When completely installed, as described below, the extension 352b is partially surrounded by a constricted portion 410b of the oblong aperture 410.

Figure 9C:
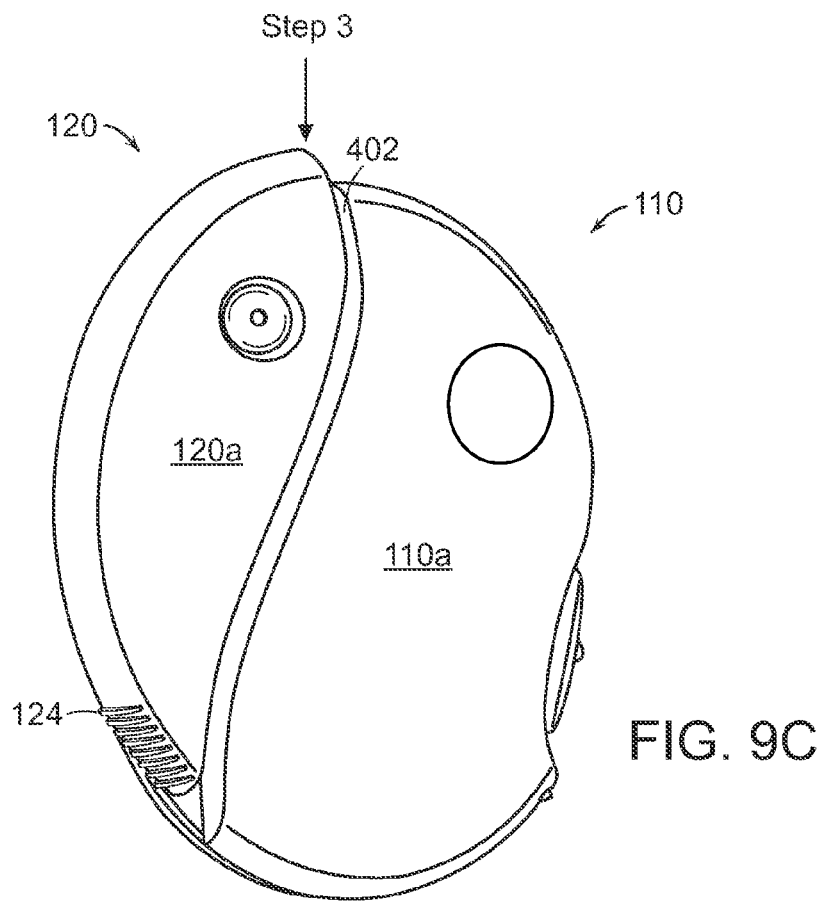
Figure 9D:
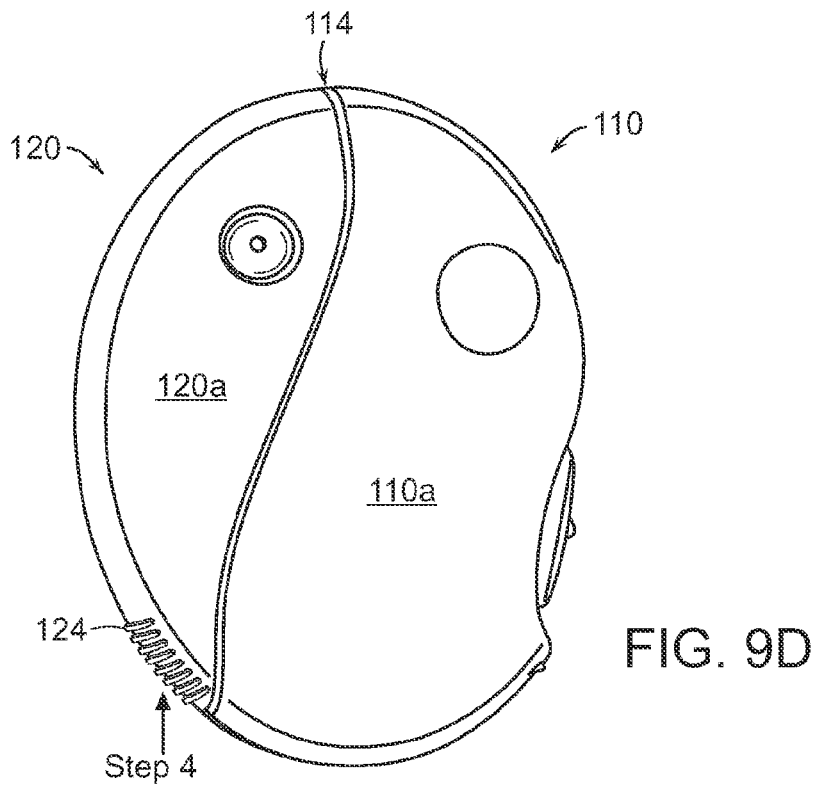

The patient attachment unit 110 and the indicator unit 120 may be secured to and detached from one another as depicted in FIGS. 9A-9D. First, from the initial position depicted in FIG. 9A, the indicator unit 120 is inverted (Step 1) such that the bottom surface 120b is arranged substantially opposite the mounting platform 404, as depicted in FIG. 9B. The indicator unit 120 is then placed (Step 2) in close proximity to the patient attachment unit 110, such that the enlarged ends 352a of the circular mating projections 352 are aligned with and pass through the enlarged portions 410a of the apertures 410. To completely secure the indicator unit 120 to the patient attachment unit 110, the patient slides (Step 3) the indicator unit 120 in an chordal direction, so that the extensions 352b of the mating projections 352 are located within the constricted portion 410b of the apertures 410. The enlarged ends 352a prevent the indicator unit 120 from being inadvertently dislodged from the patient attachment unit 110. To disconnect the indicator unit 120 from the patient attachment unit 110, the patient slides (Step 4) the indicator unit 120 in a direction opposite the direction of Step 3. Textured edge 124 may provide a gripping surface to facilitate this step. The enlarged ends 352a are again aligned with the enlarged portions 410a of the apertures 410, and the two units 110, 120 may be separated.

The indicator unit 120 may be disconnected from the patient attachment unit 110 in response to an occlusion event in the patent attachment unit 110, or due to an electronics failure or low battery charge within the indicator unit 120. Additionally, the two units 110, 120 may be disconnected because insulin in the patient attachment unit 110 may be exhausted or functionally depleted after prolonged use. In general, this may occur after a period of time defined at least in part by the volume of the elastomer reservoir 252 or the amount of insulin introduced to the reservoir 252 during filling. In certain embodiments, the elastomer reservoir, when fully filled with insulin, may contain sufficient insulin to dispense as needed for about 24, about 48, about 72, or greater than about 72 hours. Other times are also contemplated, based on the type of medicament being delivered, elastomer reservoir size, delivery schedule, etc. The separate indicator unit 120 alerts the patient when insufficient levels of insulin remain in the patient attachment unit 110. When the insulin supply in the elastomer reservoir 252 is exhausted or functionally depleted, the indicator unit 120 may be disconnected from the patient attachment unit 110 and the patient attachment unit 110 may be disposed of. Another patient attachment unit 110 may be obtained, filled with insulin and connected to the separate indicator unit 120, which may be re-used as long as it has sufficient battery power. Alternatively, the exhausted or functionally depleted patient attachment unit 110 may be refilled via the fill port 252.

Figure 10:
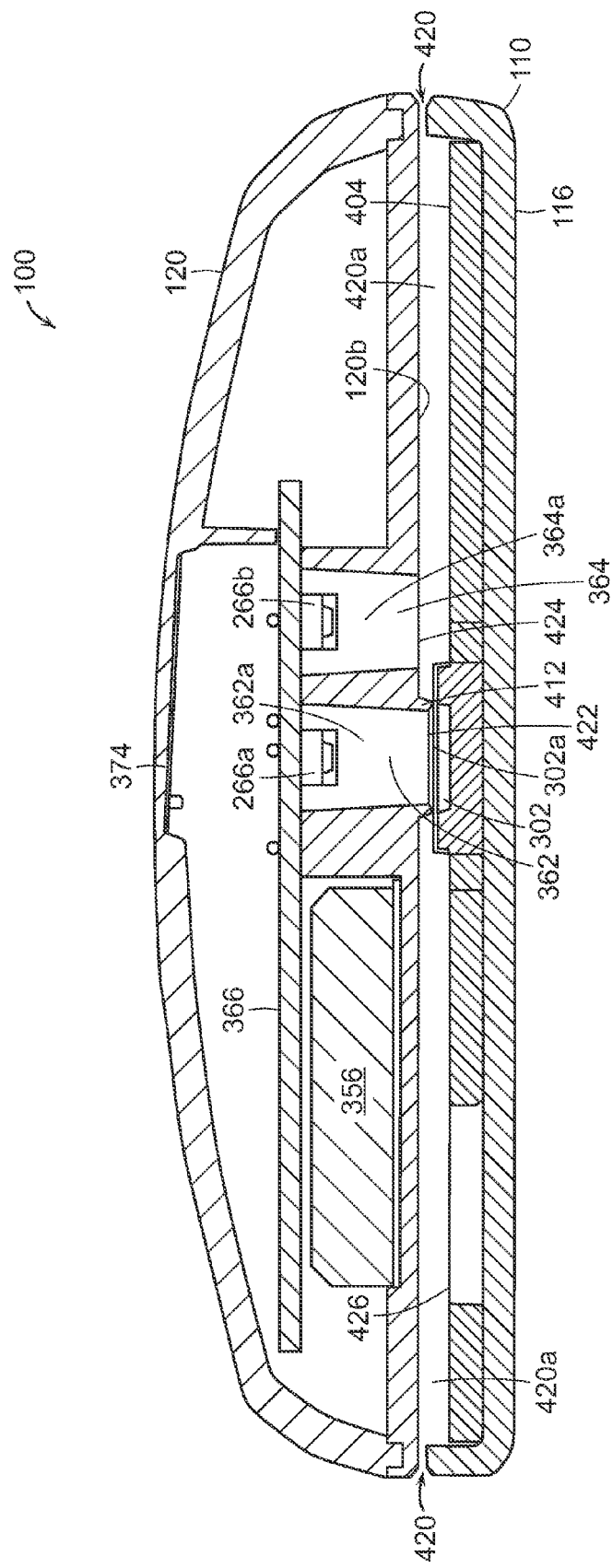
FIG. 10 is a schematic section view of the fluid medicament delivery device of FIG. 1 taken along line 10-10.

Depicted in FIG. 10 is a cross-sectional view of the assembled fluid medicament delivery device 100, depicting a number of internal components, including the piezoelectric sounder 374, the PCB 366, the battery 356, and the wells 362, 364. For clarify, many of the various conduits and components contained within the patient attachment unit 110 are not depicted. This figure is used to show the general mating relationship between the two units 110, 120. When the indicator unit 120 is secured to the patient attachment unit 110, the bottom surface 120b of the indicator unit 120 is in close proximity but slightly spaced from the mounting platform 404, with the exception of the raised lip 412 of the well 362. The raised lip 412 of the well 362 contacts the sensor membrane 302a of the patient attachment unit 110. In alternative embodiments, other portions of the bottom surface 120b may contact the mounting platform 404. The pressure sensors 266A, 266B are mounted to the PCB 366 and disposed in the wells 362, 364, respectively. Each well is filled with a substance to transmit effectively pressure, for example, a solid resilient gel 362a, 364a manufactured of silicone gel, for example, as manufactured by Dow Corning Corporation as product no. 3-4241. In general, silicone gels having a shore hardness of about 60 Shore 00 will produce satisfactory results. Other gels may also be utilized. During manufacture, to prevent leakage of the gel at the interface of the PCB 366 and wall of the wells 362, 364, a portion of the gel 362a is placed in each well 362, 364, and allowed to solidify. The remainder of the wells 362, 364 is then completely filled with the gel 362a, which is, in turn, allowed to harden. A meniscus 422 of the gel 362a in the well 362 extends to the edge of the raised lip 412. Accordingly, when the patient attachment unit 110 and the indicator unit 120 are connected, the meniscus 422 of the gel 362a contacts the sensor membrane 302a. The contact between the gel 362a and sensor membrane 302a allows both to move in relation to one another. As fluid pressure increases within the pressure chamber 302, the sensor membrane 302a is forced against the meniscus 422. This pressure is transmitted through the gel 362a to the sensor 266A. In an alternative manufacturing process, the wells 362 may be inverted and filled from the underside, with the PCB 366 placed on the wells 362 prior to curing of the gel.

Also shown in FIG. 10 is an ambient air channel 420, which is formed when the indicator unit 120 is attached to the patient attachment unit 110. Since the mounting platform 404 and the bottom surface 120b are generally not in contact, ambient air pressure may be transmitted freely into an interstitial space 420a between the two units 110, 120. This exposes both a surface or meniscus 424 of the gel 364a in the well 364 and the pressure equalizing membrane 426 to ambient air pressure P external to the device 100. This allows the device 100 to sense changes in ambient air pressure, as described below.

Figure 11:
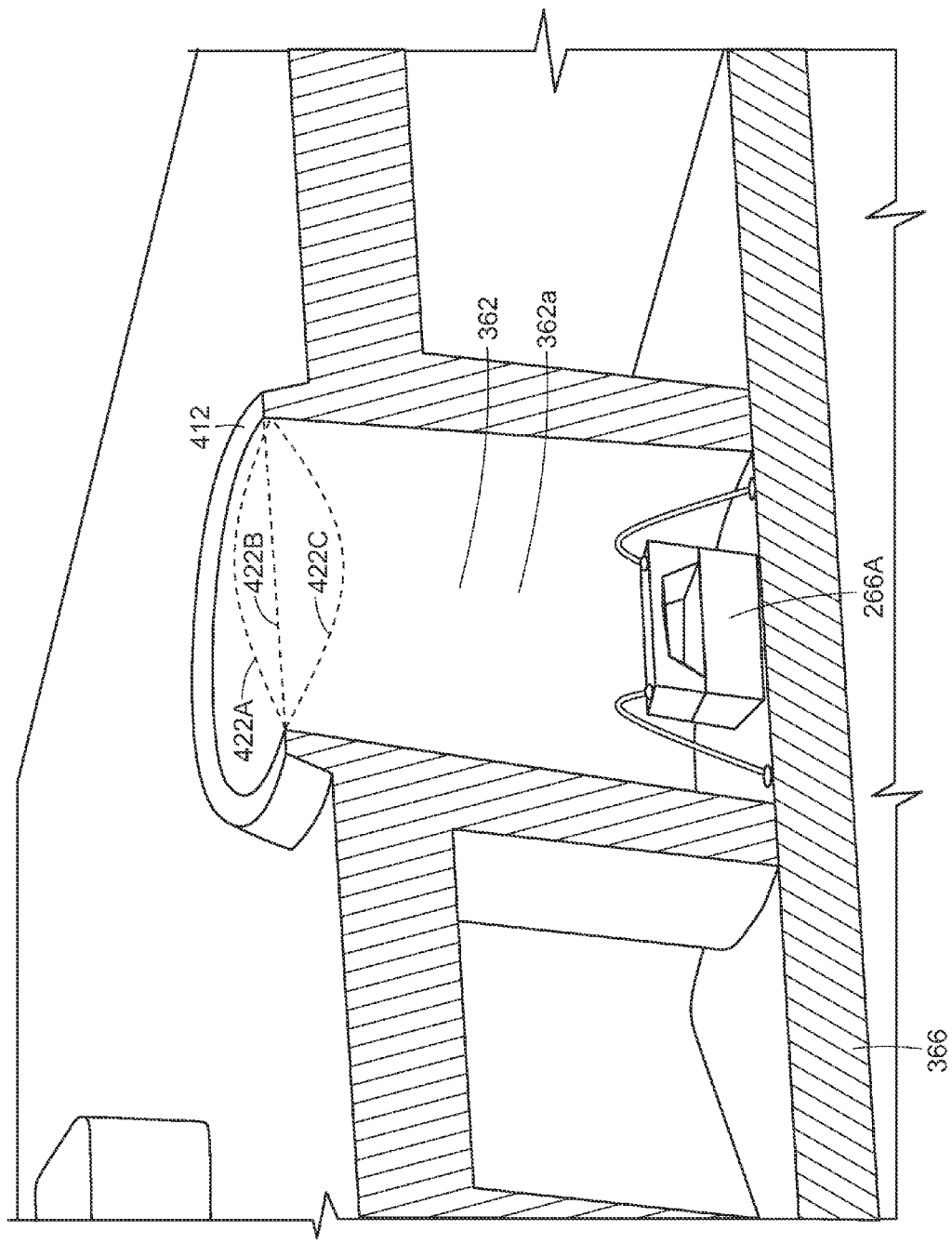
FIG. 11 is a partial schematic section view of a well of FIG. 8 taken along line 11-11.

FIG. 11 depicts an enlarged inverted cross-sectional view of the well 362. The pressure sensor 266A is mounted on the PCB 366 at the base of the well 362. As described above, the gel 362a is filled to the edge of the raised lip 412. Three dashed lines 422A, 422B, and 422C illustrate the meniscus 422 of the gel 362a according to various conditions. Line 422A illustrates over-filling of the gel 362a; line 422B illustrates desired filling of the gel 362a; line 422C illustrates under-filling of the gel 362a. When the gel 362a is filled to the desired level (i.e., coplanar with the raised lip 412) the meniscus 422B is proximate with the sensor membrane 302a, while transferring little or no force between the two elements. Force transmission remains minimal or nonexistent until fluid fills the pressure chamber 302. The raised lip 412 minimizes the initial distance between the meniscus 422B and the sensor membrane 302a. If the gel 362a has been over-filled, the meniscus 422A may exert force on the sensor membrane 302a, which may lead to inaccurate sensing. If the gel 362a has been under-filled, the sensor membrane 302a may not contact the meniscus 422C, again leading to inaccurate sensing.

Figure 12:
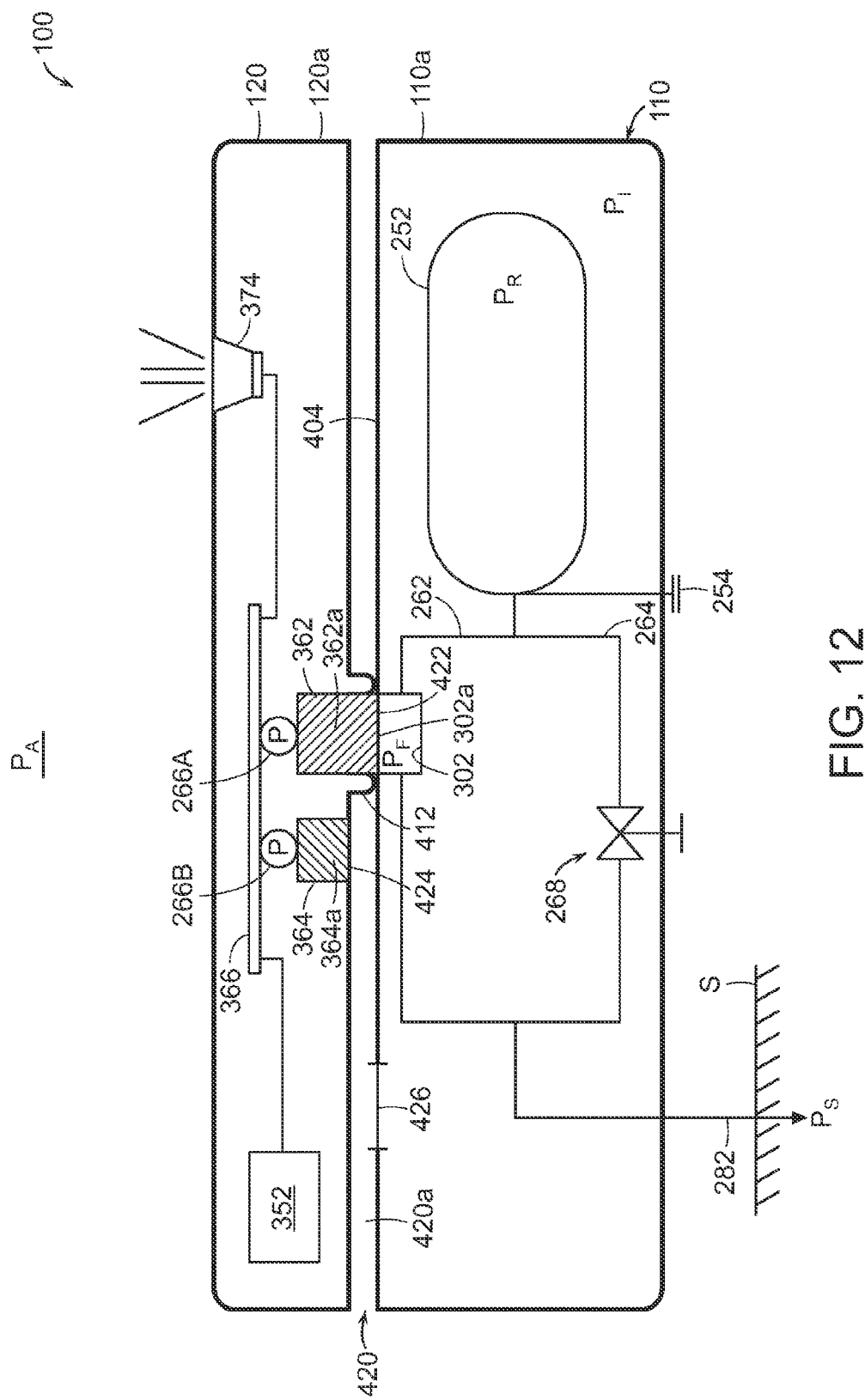
FIG. 12 is a schematic section view of a fluid medicament delivery device in accordance with another embodiment of the present invention.

FIG. 12 depicts a simplified, schematic view of the fluid medicament delivery device 100 to illustrate the interrelationships between, as well as the functionality of, the various components according to one embodiment of the device 100. The patient attachment unit 110 includes a simplified, schematic version of the micro-fluidic circuit depicted in FIG. 3, contained within the housing 110a. The flexible pressure equalizing membrane 426 is disposed within and substantially coterminous with the mounting platform 404. The patient attachment unit 110 includes the reservoir 252, for example, an elastomer bladder. The fill port 254 may be used to introduce insulin into the reservoir 252. Insulin displaced from the reservoir 252 fills the basal flowpath 262 and the bolus flowpath 264. Insulin flows through the bolus flowpath 264 and into the patient via the cannula 282 when the bolus button 268 is actuated. Insulin in the basal flowpath 262 flows through the pressure sensor chamber 302, which includes a sensor membrane 302a, which is substantially coterminous with the top portion of the mounting platform 404 of the patient attachment unit 110. Insulin from the basal flowpath 262 and bolus flowpath 264 is introduced subcutaneously into the patient via the cannula 282.

The simplified, schematic version of the indicator unit 120 includes the PCB 366, which is powered by the battery 352. The piezoelectric sounder 374 and/or a light, such as a LED, is connected to the PCB 366. Also mounted on the PCB 366 are the pressure sensors 266A, 266B, which are each disposed in the wells 362, 364, respectively. The well 364 depicted on the right in FIG. 12 includes the raised lip 412. Each well 362, 364 is filled with the gel 362a, 364a, such that the meniscus 422, 424 is formed thereon.

When the indicator unit 120 is attached to the patient attachment unit 110, the ambient air channel 420 and the interstitial space 420a is formed therebetween. Note that the various connecting elements are not depicted. Both the meniscus 424 of the gel 364a and the flexible pressure equalizing membrane 426 of the patient attachment unit 110 are exposed to the ambient pressure $P_A$ in the interstitial space 420a.

As insulin in the basal flowpath 262 flows through the pressure sensor chamber 302, when insulin pressure is greater than ambient pressure, the insulin in the filled pressure sensor chamber 302 will flex the sensor membrane 302a outwards. This outward deflection will, in turn, apply pressure to the meniscus 422 of the gel 362a, thus transmitting that pressure to pressure sensor 266A. The PCB 366 interprets the pressure increase and, if required, alerts the patient, e.g., via the piezoelectric sounder 374 and/or the light.

Changes in pressure conditions in the basal flowpath that may occur for at least several reasons: (1) due to an occlusion or partial occlusion downstream of the pressure sensor chamber 302; (2) due to an occlusion or partial occlusion upstream of the pressure sensor chamber 302; or (3) due to a pressure spike inherent in the last phase of contraction of the elastomer reservoir 252. An occlusion or partial occlusion causes the basal flow to stop or partially stop. A pressure spike from the elastomer reservoir 252 occurs when the reservoir 252 is approaching the limit of the reservoir's ability to continue the flow of insulin. During contraction, the elastomer reservoir 252 maintains a substantially constant pressure on the insulin delivered via the basal flowpath 262. However, as the reservoir 252 nears its fully contracted state, the wall applies move force to the insulin, temporarily increasing the pressure until the wall achieves a final rest condition and the insulin pressure equalizes with that of the subcutaneous pressure of the patient. These pressure relationships are described in more detail below.

The indicator unit 120 may be programmed to conduct a pressure reading periodically, for example, about every 30 minutes, to monitor the function of the fluid medicament delivery device 100. This allows for low power consumption and provides for longer life of the battery 352. Periodic pressure readings allow the indicator unit 120 to alert the patient to, and differentiate between, a change in fluid pressure caused by occlusions/partial occlusions and a change in fluid pressure caused by the last contraction phase of the elastomer reservoir 252. As described in more detail below, the electronic components contained within the indicator unit 120 may determine that a change in pressure during the early operational life of the device 100 is due to an occlusion (e.g., a blocked cannula 282). Further, the indicator unit 120 may determine that a change in pressure during the late stages of operation of the device 100 is due to the last contraction phase of the elastomer reservoir 252. Regardless, upon detection of a pressure change of a predetermined threshold valve, the patient will be alerted that the device 100 is not working properly and that the patient attachment unit 110 needs to be replaced.

The fluid medicament delivery device 100 may operate properly in various external pressure environments, for example, while a patient is at sea-level, at elevated pressure conditions (i.e., below sea-level), and at decreased pressure conditions (i.e., above sea-level). Additionally, due to the functionality described below, the components contained within the indicator unit 120 are able to distinguish pressure changes caused by occlusions from those caused by changes in ambient pressure. The fluid medicament delivery device 100 will continue operating normally in various external pressure environments and, thus, alert the patient to changes in pressure that are only due to conditions that require attention to the device 100 (e.g., an occlusion, a partial occlusion, or a near-empty condition of the elastomer bladder 252).

As described above, the indicator unit 120 includes two pressure sensors 266A, 266B that are both absolute pressure sensors. When the indicator unit 120 and patient attachment unit 110 are connected, the pressure sensor 266B is exposed to ambient air pressure $P_A$. Table 1 depicts known conditions for ambient pressure $P_A$, subcutaneous (below the skin surface S) pressure $P_S$ of a human body, and reservoir pressure $P_R$. These pressures are given at sea-level, 1 meter below sea-level, and 3000 meters above sea-level. As an initial matter, due to the presence of the pressure equalizing membrane 426, the ambient pressure $P_A$ equals the device internal pressure $P_I$. The human body is also pressurized relative to the ambient air pressure $P_A$, such that the subcutaneous pressure $P_s$ of the human body may be calculated as a combination of the ambient pressure and about 10 mbar. The reservoir pressure $P_R$ exerted against the fluid contained therein may be calculated as the combination of the internal device pressure $P_I$ and about 820 mbar (i.e., the pressure exerted directly against the fluid by the elastomer bladder material). The pressure exerted by the elastomer bladder material may be greater than or less thank 820 mbar, depending on the material used.

TABLE 1

Known Pressures for Use in Device Operation

| All pressures in mbar | Ambient Pressure $P_A = P_I$ | Subcutaneous Pressure $P_S = P_A + 10$ | Reservoir Pressure $P_R = P_I + 820$ |
|---|---|---|---|
| Pressure at Sea-Level | 1013 | 1023 | 1833 |
| Pressure at 1.0 meter submersion | 1113 | 1123 | 1933 |
| Pressure at 3000 meters altitude | 800 | 810 | 1620 |

Further, the fluid pressure $P_F$ is sensed at pressure sensor 266A because the meniscus 422 of the gel 362a contacts the sensor membrane 302a of the pressure sensor chamber 302 through which the insulin flows. Table 2 depicts fluid pressures $P_F$ at sea-level, 1 meter below sea-level, and 3000 meters above sea-level. Under Normal (i.e., unblocked) conditions, the fluid pressure $P_F$ at the pressure sensor 266A is the average of the subcutaneous pressure $P_s$ and the reservoir pressure $P_R$. Table 2 also depicts fluid pressure $P_F$ at complete occlusion and partial occlusion (so-called "half-blocking") conditions both upstream and downstream of the pressure sensor chamber 302. Half-blocking conditions may occur when a flow channel or a flow restrictor has a partial occlusion, allowing passage of inclusion at only one-half of its rated flow rate.

TABLE 2

Fluid Pressures at Operational Conditions

| All pressures in mbar | Normal $P_F = (P_S + P_R)/2$ | Upstream Occlusion $P_F = P_S$ | Upstream Half-blocking $P_F = (2*P_S + P_R)/3$ | Downstream Occlusion $P_F = P_R$ | Downstream Half-blocking $P_F = (P_S + 2*P_R)/3$ |
|---|---|---|---|---|---|
| Pressure at Sea-Level | 1428 | 1023 | 1293 | 1833 | 1563 |
| Pressure at 1.0 meter submersion | 1528 | 1123 | 1393 | 1933 | 1663 |
| Pressure at 3000 meters altitude | 1215 | 810 | 1080 | 1620 | 1350 |

Table 3 depicts pressure differentials ΔP at sea-level, 1 meter below sea-level, and 3000 meters above sea-level. Generally, a Normal pressure differential ΔP may be about 450 mbar +/−about 15%. In one embodiment, a pressure differential ΔP between fluid pressure $P_F$ and ambient pressure $P_A$ from about 344 mbar to about 517 mbar at, below, or above sea-level, is considered normal. A pressure differential ΔP below about 344 mbar is considered a first failure state, generally caused by an upstream (of the pressure sensor chamber 302) occlusion, partial occlusion, or near-empty elastomer bladder condition. A pressure differential ΔP above about 517 mbar is considered a second failure state, generally caused by a downstream (of the pressure sensor chamber 302) occlusion or partial occlusion. The uniform pressure differentials for each failure condition (i.e., upstream and downstream occlusion, upstream and downstream half-blocking) allow the device to differentiate between the various failure conditions. Information regarding the various failure conditions may be stored in the components within the indicator unit 120, for later download to a computer for device-diagnostic or other purposes.

TABLE 3

Pressure Differentials at Operational Conditions

| All pressures in mbar | Normal $\Delta P = P_F - P_A$ | Upstream Occlusion $\Delta P = P_F - P_A$ | Upstream Half-blocking $\Delta P = P_F - P_A$ | Downstream Occlusion $\Delta P = P_F - P_A$ | Downstream Half-blocking $\Delta P = P_F - P_A$ |
|---|---|---|---|---|---|
| Pressure at Sea-Level | 415 | 10 | 280 | 820 | 550 |
| Pressure at 1.0 meter submersion | 415 | 10 | 280 | 820 | 550 |
| Pressure at 3000 meters altitude | 415 | 10 | 280 | 820 | 550 |

The pressure-equalizing membrane 426 allows the device to accurately sense pressures and analyze the various pressure conditions during operation, either at, above, or below sea-level. Consider a proposed insulin infusion device that lacks a pressure equalizing membrane (depicted as 426 in FIG. 12). Table 4 depicts known conditions for ambient pressure $P_A$, internal device pressure $P_I$, subcutaneous pressure $P_S$ of a human, and reservoir pressure $P_R$. These pressures are given at sea-level, 1 meter below sea-level, and 3000 meters above sea-level. Since a pressure equalizing membrane is not utilized, the internal device pressure $P_I$ remains constant (in this case, at the environmental pressure at which the device was manufactured, e.g., sea-level). In certain devices, the internal pressure $P_I$ may be elevated, if the device was manufactured in a clean room, for example, which typically has a pressure higher than the ambient pressure of the location where the clean room is contained. Regardless, this constant internal pressure $P_I$ has a direct effect on the reservoir pressure $P_R$, as shown in Table 4.

TABLE 4

Known Pressures for Use in Device Operation
(No Pressure-Equalizing Membrane)

| All pressures in mbar | Ambient Pressure $P_A$ | Internal Pressure $P_I$ | Subcutaneous Pressure $P_S = P_A + 10$ | Reservoir Pressure $P_R = P_I + 820$ |
|---|---|---|---|---|
| Pressure at Sea-Level | 1013 | 1013 | 1023 | 1833 |
| Pressure at 1.0 meter submersion | 1113 | 1013 | 1123 | 1833 |
| Pressure at 3000 meters altitude | 800 | 1013 | 810 | 1820 |

Table 5 depicts fluid pressures $P_F$ at sea-level, 1 meter below sea-level, and 3000 meters above sea-level, for a device lacking a pressure-equalizing membrane. Fluid pressure $P_F$ at complete occlusion and partial occlusion conditions upstream and downstream of the pressure sensor chamber 302 are also depicted in Table 5.

TABLE 5

Fluid Pressures at Operational Conditions (No Pressure-Equalizing Membrane)

| All pressures in mbar | Normal $P_F = (P_S + P_R)/2$ | Upstream Occlusion $P_F = P_S$ | Upstream Half-blocking $P_F = (2*P_S + P_R)/3$ | Downstream Occlusion $P_F = P_R$ | Downstream Half-blocking $P_F = (P_S + 2*P_R)/3$ |
|---|---|---|---|---|---|
| Pressure at Sea-Level | 1428 | 1023 | 1293 | 1833 | 1563 |
| Pressure at 1.0 meter submersion | 1478 | 1123 | 1360 | 1833 | 2395 |
| Pressure at 3000 meters altitude | 1322 | 810 | 1151 | 1833 | 1492 |

Table 6 depicts pressure differentials ΔP at sea-level, 1 meter below sea-level, and 3000 meters above sea-level. As described above, a Normal pressure differential ΔP may be defined as about 450 mbar +/−about 15%. That is, a pressure differential ΔP from about 344 mbar to about 517 mbar at, below, or above sea-level is considered normal. A pressure differential ΔP below about 344 mbar is considered a first failure state; a pressure differential ΔP above about 517 mbar is considered a second failure state. The pressure differentials depicted in Table 6 show the advantages provided by a infusion device that includes a pressure-equalizing membrane, such as that used with the device described herein. Absence of the pressure equalizing membrane may cause at least three types of problems. First, pressure differentials under Normal (i.e., unblocked) conditions may register as a failure condition (where a failure condition is defined as a pressure differential in excess of 517 mbar). See, for example, the Normal condition pressure at 3000 meters altitude, which is an operational altitude for an airplane. In such a case, the device is operating normally, but the device interprets the pressure differential as a failure condition. The device would signal the patient that the device is not operating properly, which may cause the patient to remove and replace a device that is otherwise operating properly.

Second, a condition that should be interpreted as a failure condition may be overlooked. See, for example, the Upstream Half-blocking condition pressure at 3000 meters altitude. There, the pressure differential falls within the normal range of about 344 mbar to 517 mbar. Thus, the device would not alert the patient to a failure conditions, even though there is blockage within the fluid circuit. This may cause a serious medical condition. Third, as can be seen, the pressure differentials are not consistent across the same failure conditions, which would prevent the particular failure condition from being subsequently identified during diagnostics.

delivery device 100 includes the patient attachment unit 110 and the separate indicator unit 120. A housing for the cannula insertion device 450 and the bolus button 268 are disposed on the patient attachment unit 110. An adhesive tape 452 for adhering the device 100 to the skin of a patient is disposed on the underside of the patient attachment unit 110. A liner 454 is included to cover the adhesive tape 452 before the device 100 is attached to the patient.

The device 100 is first removed its packaging (Step 500) which keeps the device 100 clean during storage and transport, prior to use. The separate indicator unit 120 is mounted to the patient attachment unit 100 (Step 502), for example, in the manner described above and shown in FIGS. 9A-9C. To fill the device 100 with insulin (Step 504), an insulin pen 254a is connected to a fill port 254 on the underside of the patient attachment unit 110. Insulin is then dispensed from the pen 254a to fill the insulin reservoir (Step 506). Once full, the insulin pen 254a is disconnected from the device 100 and discarded (Step 508). The liner 454 is then removed from the device 100 to expose the adhesive tape (Step 510). The patient attachment unit 100 is then adhered to an appropriate portion of the patient's skin S (Step 512). Acceptable locations include, but are not limited to, the abdominal area, the area above the buttocks, or the area proximate the triceps muscle. The patient then actuates the cannula insertion device 450 to insert the cannula into the body (Step 514). The patient disconnects the housing of the cannula insertion device 450 from the patient attachment unit 110 (Step 516). The device 100 is now operational and may be worn by the patient during normal, everyday activities. When the device 100 needs to be removed (either due to a failure state or depletion of insulin), the patient peels the device 100 from the skin S (Step 518). As shown in Step 520, the patient may then detach the indicator unit 120 from the patient attachment unit 110, as described above with regard to FIG. 9D. The indicator unit 120 may

TABLE 6

Pressure Differentials at Operational Conditions (No Pressure-Equalizing Membrane)

| All pressures in mbar | Normal $\Delta P = P_F - P_A$ | Upstream Occlusion $\Delta P = P_F - P_A$ | Upstream Half-blocking $\Delta P = P_F - P_A$ | Downstream Occlusion $\Delta P = P_F - P_A$ | Downstream Half-blocking $\Delta P = P_F - P_A$ |
|---|---|---|---|---|---|
| Pressure at Sea-Level | 415 | 10 | 280 | 820 | 550 |
| Pressure at 1.0 meter submersion | 365 | 10 | 247 | 720 | 1282 |
| Pressure at 3000 meters altitude | 522* | 10 | 351* | 1033 | 692 |

Figure 13A:
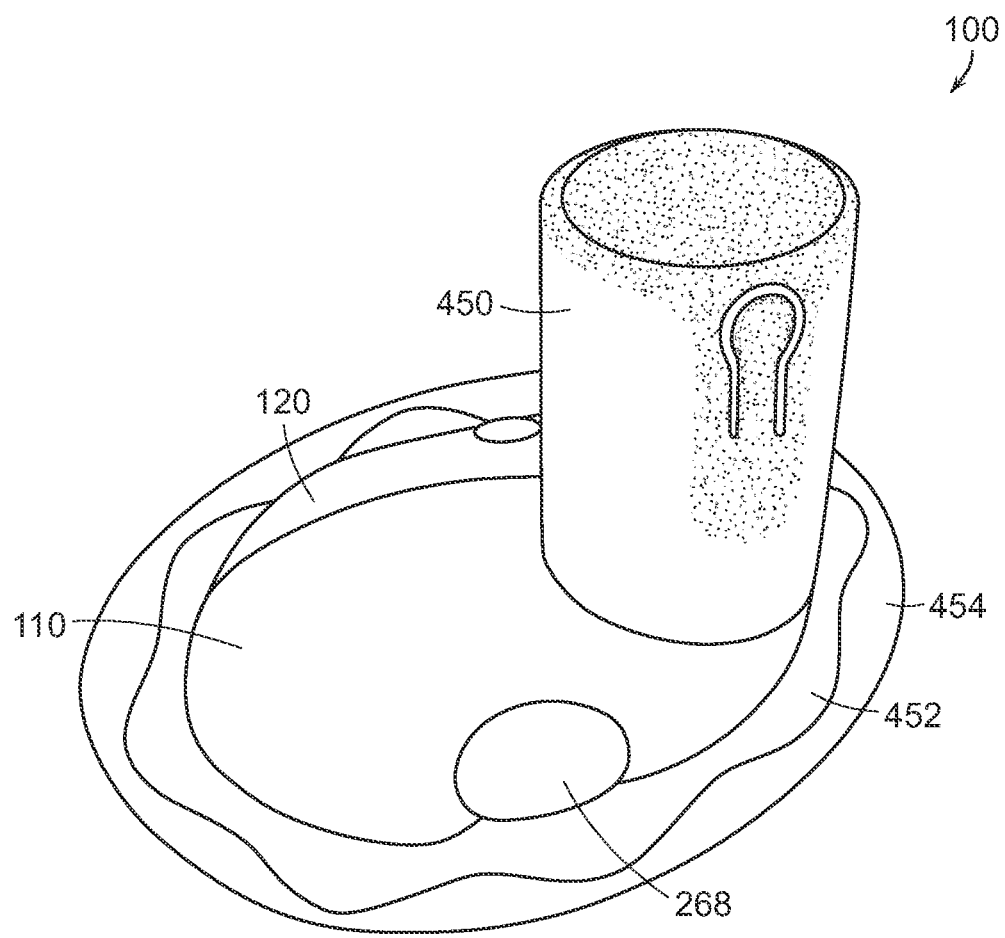
FIGS. 13A-13C depict a procedure for utilizing a fluid medicament delivery device in accordance with one embodiment of the present invention.
Figure 13B:
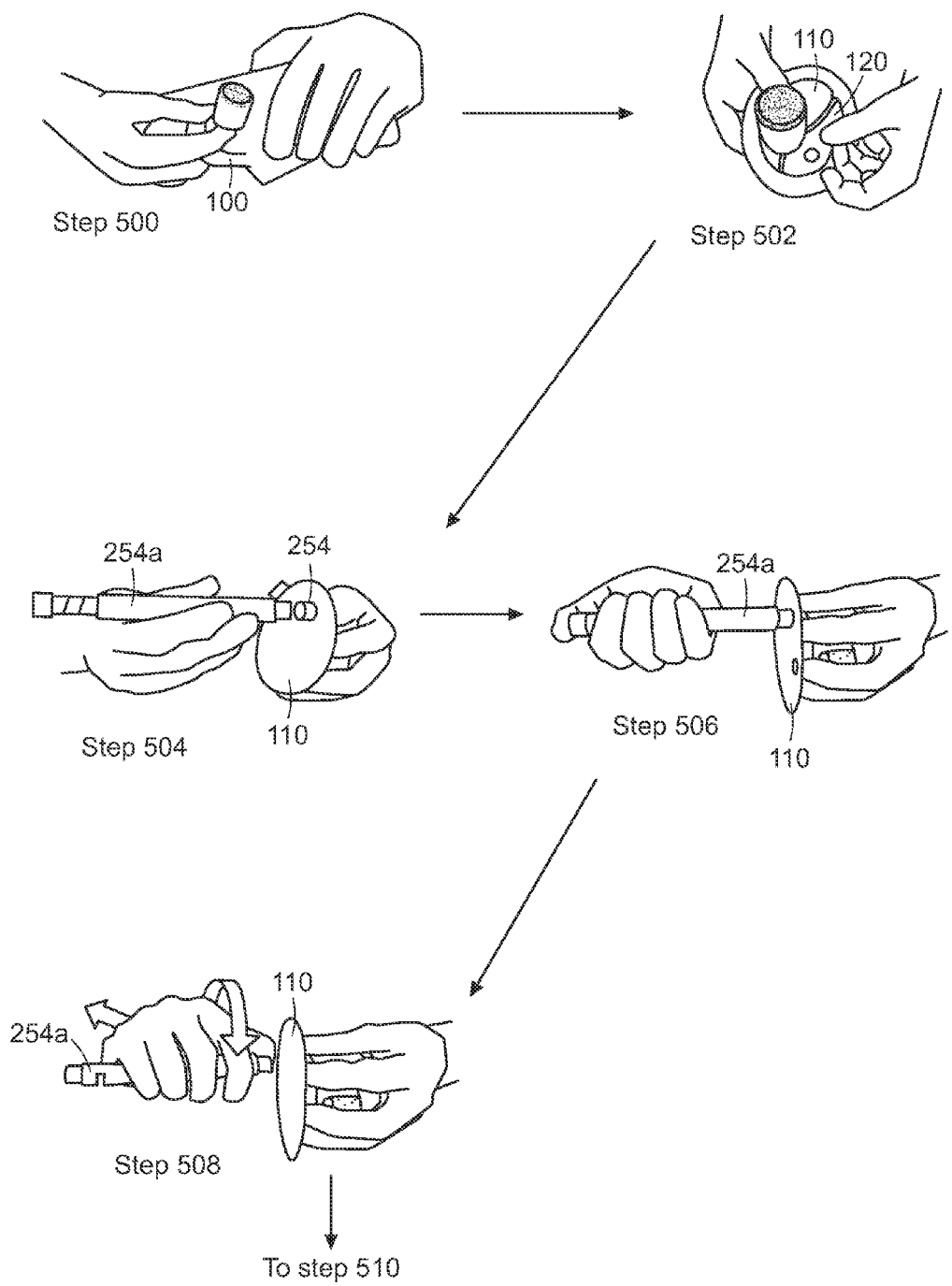
Figure 13C:
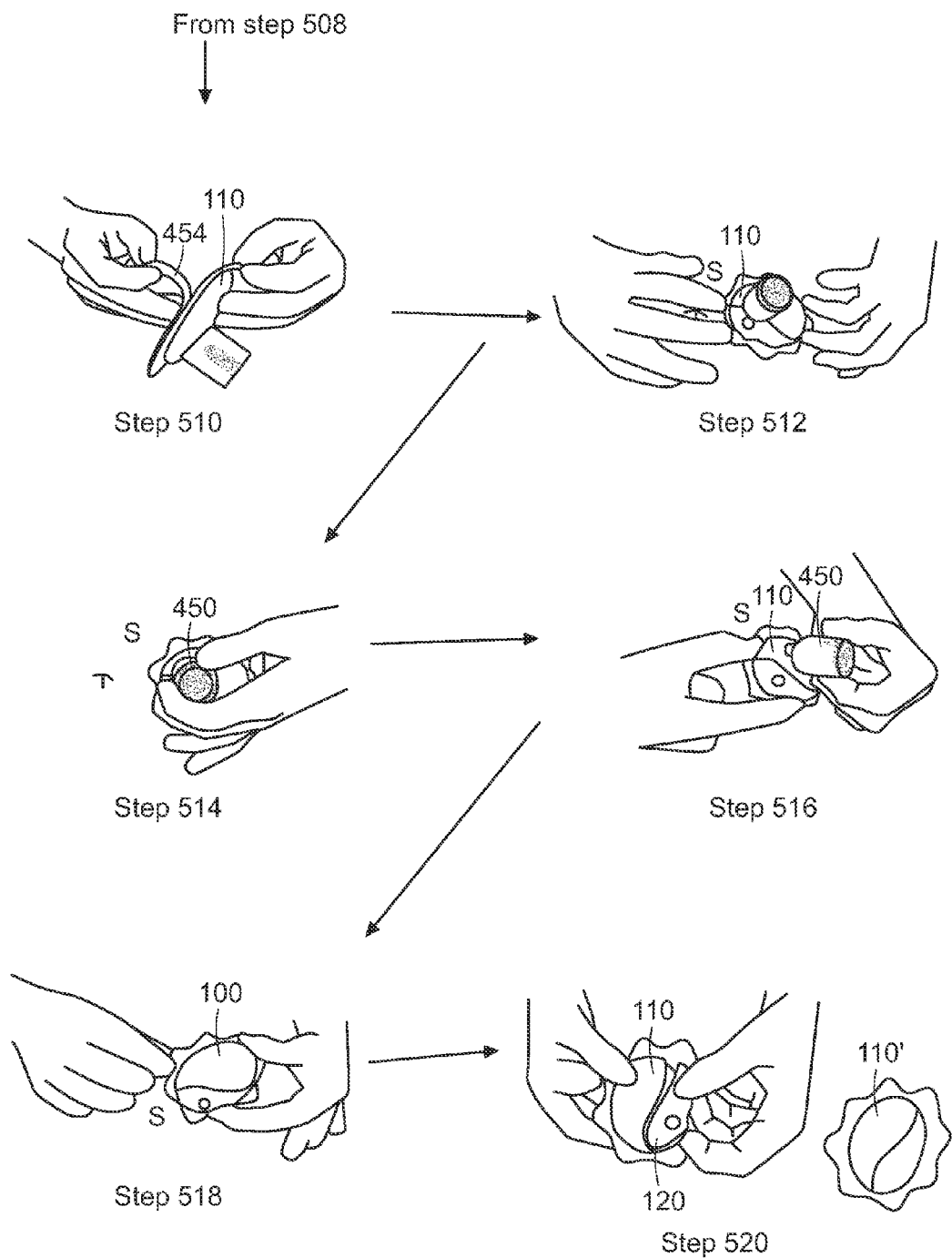

FIG. 13A depicts a perspective view of a fluid medicament delivery device 100 in accordance with an embodiment of the invention. FIGS. 13B-13C depict a procedure for using the fluid medicament delivery device 100. The fluid medicament then be attached to a new patient attachment unit 110'. In this way, the comparatively more-expensive indicator unit 120 may be reused, while the less-expensive patient attachment unit 110 may be disposed of.

The various components utilized in the device described herein may be metal, glass, and/or any type of polymer suitable for sterilization and useful for delivering insulin or other medicaments subcutaneously. Polyurethane, polypropylene, PVC, PVDC, EVA, and others, are contemplated for use, as are stainless steel and other medical-grade metals. More specifically, medical-grade plastics may be utilized for the cannula itself, as well as other components that contact or otherwise penetrate the body of the patient. Needles and springs made from medical-grade stainless steel are also desirable, to prevent failure associated with use.

While there have been described herein what are to be considered exemplary and preferred embodiments of the present invention, other modifications of the invention will become apparent to those skilled in the art from the teachings herein without departing from the spirit or essential characteristics thereof. The present embodiments are therefore to be considered in all respects as illustrative and not restrictive. The particular methods of manufacture and geometries disclosed herein are exemplary in nature and are not to be considered limiting. It is therefore desired to be secured in the appended claims all such modifications as fall within the spirit and scope of the invention. Accordingly, what is desired to be secured by Letters Patent is the invention as defined and differentiated in the following claims, and all equivalents.

The invention claimed is:

1. A fluid medicament delivery device comprising:
 a patient attachment unit comprising a housing and a fluid channel located therein, wherein at least a portion of the fluid channel comprises a flexible member substantially coterminous with the housing;
 a separate indicator unit adapted to be detachably coupled to the housing of the patient attachment unit, the indicator unit comprising a first sensing element for contacting the flexible member when the indicator unit is coupled to the housing, wherein the first sensing element senses a flexure of the flexible member; and
 a equalizing membrane exposed to an ambient pressure external to the housing, wherein the equalizing membrane is adapted for enabling analysis of various pressure conditions during operation at different ambient pressures.

2. The fluid medicament delivery device of claim 1, wherein the indicator unit further comprises a second sensing element for sensing the ambient pressure.

3. The fluid medicament delivery device of claim 2, wherein the second sensing element comprises a pressure sensor adapted to sense the ambient pressure, and at least one of a fluid and a gel adapted to transmit the ambient pressure to the pressure sensor.

4. The fluid medicament delivery device of claim 1, wherein the first sensing element comprises a pressure sensor.

5. The fluid medicament delivery device of claim 4, wherein the first sensing element further comprises at least one of a fluid and a gel adapted to contact the flexible member, wherein the flexure of the flexible member is transmitted by the at least one of the fluid and the gel to the pressure sensor.

6. The fluid medicament delivery device of claim 5, wherein the separate indicator unit defines a well for containing at least one of the liquid and the gel.

7. The fluid medicament delivery device of claim 6, wherein the separate indicator unit comprises a raised lip surrounding the well, wherein the raised lip is disposed above a proximate portion of the separate indicator unit.

8. The fluid medicament delivery device of claim 7, wherein the raised lip is adapted to contact the housing of the patient attachment unit.

9. The fluid medicament delivery device of claim 1, wherein the housing comprises a hermetically-sealed housing defining an interior space and comprising the equalizing membrane, the equalizing membrane adapted for transmitting the ambient pressure to the interior space.

10. The fluid medicament delivery device of claim 9, wherein the equalizing membrane is located on a portion of the patient attachment unit facing the separate indicator unit and wherein the second sensing element is located on a portion of the separate indicator unit facing the patient attachment unit, when the patient attachment unit is coupled to the separate indicator unit.

11. The fluid medicament delivery device of claim 1, wherein the patient attachment unit is adapted for adhesion to a skin surface of a patient.

12. The fluid medicament delivery device of claim 1, further comprising a processor adapted for interpreting a signal from a pressure sensor, wherein the signal is sent to the processor based at least in part on the flexure of the flexible member.

13. A method of monitoring pressure within a fluid channel of a fluid medicament delivery device, the method comprising:
 measuring an actual pressure of a fluid within the fluid channel across a flexible member;
 equalizing an ambient pressure external to the device and an internal pressure across a equalizing membrane;
 measuring the ambient pressure external to the device;
 calculating a pressure differential based on the actual pressure and the ambient pressure;
 comparing the pressure differential to a pressure range comprising a maximum pressure differential and a minimum pressure differential; and
 sending a notification when the pressure differential is outside of the pressure range.

14. The method of claim 13, further comprising:
 modifying the pressure differential based on the ambient pressure to obtain a corrected pressure differential; and
 comparing the corrected pressure differential to the pressure range.

15. The method of claim 13, further comprising:
 modifying the maximum pressure differential and a minimum pressure differential of the pressure range based on the ambient pressure to obtain a corrected pressure range; and
 comparing the corrected pressure range to the pressure differential.

16. The method of claim 13, wherein when the pressure differential exceeds the maximum pressure differential, the notification comprises at least one of a downstream occlusion notification and a near-empty reservoir notification.

17. The method of claim 13, wherein when the pressure differential is less than the minimum pressure differential, the notification comprises at least one of an upstream occlusion notification and an empty reservoir notification.

* * * * *

UNITED STATES PATENT AND TRADEMARK OFFICE
CERTIFICATE OF CORRECTION

PATENT NO. : 8,672,873 B2
APPLICATION NO. : 12/542808
DATED : March 18, 2014
INVENTOR(S) : Peter Gravesen et al.

Page 1 of 1

It is certified that error appears in the above-identified patent and that said Letters Patent is hereby corrected as shown below:

In the Claims:

Column 17, claim 1, line 38, replace "a" with --an--.

Column 18, claim 13, line 32, replace "a" with --an--.

Column 18, claim 15, line 47, replace "a" with --the--.

Signed and Sealed this
Second Day of September, 2014

Michelle K. Lee
*Deputy Director of the United States Patent and Trademark Office*